United States Patent
Cai et al.

(10) Patent No.: US 9,110,055 B2
(45) Date of Patent: Aug. 18, 2015

(54) NANOSCALE SENSORS

(75) Inventors: Dong Cai, Cambridge, MA (US); Thomas Chiles, Norfolk, MA (US); Krzysztof Kempa, Chestnut Hill, MA (US); Michael Naughton, Norwood, MA (US); Zhifeng Ren, Newton, MA (US); Paudel Trilochan, Allston, MA (US)

(73) Assignee: The Trustees of Boston College, Chestnut Hill, MA (US)

( * ) Notice: Subject to any disclaimer, the term of this patent is extended or adjusted under 35 U.S.C. 154(b) by 1613 days.

(21) Appl. No.: 12/514,689

(22) PCT Filed: Nov. 16, 2007

(86) PCT No.: PCT/US2007/024043
§ 371 (c)(1),
(2), (4) Date: Aug. 10, 2011

(87) PCT Pub. No.: WO2008/133656
PCT Pub. Date: Nov. 6, 2008

(65) Prior Publication Data
US 2011/0287977 A1 Nov. 24, 2011

Related U.S. Application Data

(60) Provisional application No. 60/859,735, filed on Nov. 17, 2006.

(51) Int. Cl.
*G01N 33/543* (2006.01)
*G01N 27/327* (2006.01)

(52) U.S. Cl.
CPC ...... *G01N 33/54346* (2013.01); *G01N 27/3278* (2013.01)

(58) Field of Classification Search
CPC ... G01N 27/00; G01N 27/028; G01N 27/221; G01N 27/226; G01N 27/227; G01N 27/228; G01N 2027/221
See application file for complete search history.

(56) References Cited

U.S. PATENT DOCUMENTS

| | | | |
|---|---|---|---|
| 6,791,757 B2 * | 9/2004 | Hobbs et al. | 359/578 |
| 7,013,708 B1 | 3/2006 | Cho et al. | |
| 7,166,325 B2 | 1/2007 | Dai | |
| 2003/0134267 A1 | 7/2003 | Kang et al. | |

(Continued)

FOREIGN PATENT DOCUMENTS

KR 102006115470 11/2006

OTHER PUBLICATIONS

Seetharamappa, Jaldappagari et al., "Carbon Nanotubes: Next Generation of Electronic Materials," Summer 2006, The Electrochemical Society Interface, pp. 23-25 and 61.*

(Continued)

*Primary Examiner* — Christopher M Gross
(74) *Attorney, Agent, or Firm* — Joseph M. Noto; Bond, Schoeneck & King PLLC

(57) ABSTRACT

A nanocoaxial sensor includes an outer conductor, an inner conductor, a dielectric material disposed between the outer and inner conductors, a nanocavity sized to allow target species to enter the nanocavity between the outer and inner conductors, and an active sensing element immobilized within the nanocavity on at least one of the inner or outer conductors. The active sensing element is adapted to selectively capture the at least one of the target species.

15 Claims, 18 Drawing Sheets

(56) References Cited

U.S. PATENT DOCUMENTS

| | | | |
|---|---|---|---|
| 2004/0104129 A1* | 6/2004 | Gu et al. | 205/775 |
| 2004/0106203 A1 | 6/2004 | Stasiak et al. | |
| 2004/0245209 A1 | 12/2004 | Jung et al. | |
| 2005/0136419 A1* | 6/2005 | Lee | 435/6 |
| 2005/0181409 A1 | 8/2005 | Park et al. | |
| 2005/0230270 A1 | 10/2005 | Ren et al. | |
| 2005/0244886 A1* | 11/2005 | Iwadate et al. | 435/6 |
| 2006/0237310 A1 | 10/2006 | Patel et al. | |

OTHER PUBLICATIONS

C.H. Choi et al., "YY1-DNA interaction results in a significant change of electronic context as measured by capacitance," Biophysical Chemistry 103, 109-115 (2003).

International Preliminary Report on Patentability for PCT/US2007/024043 dated May 19, 2009.

International Search Report for PCT/US2007/024043 dated Dec. 22, 2008.

Written Opinion for PCT/US2007/024043 dated Dec. 22, 2008.

* cited by examiner

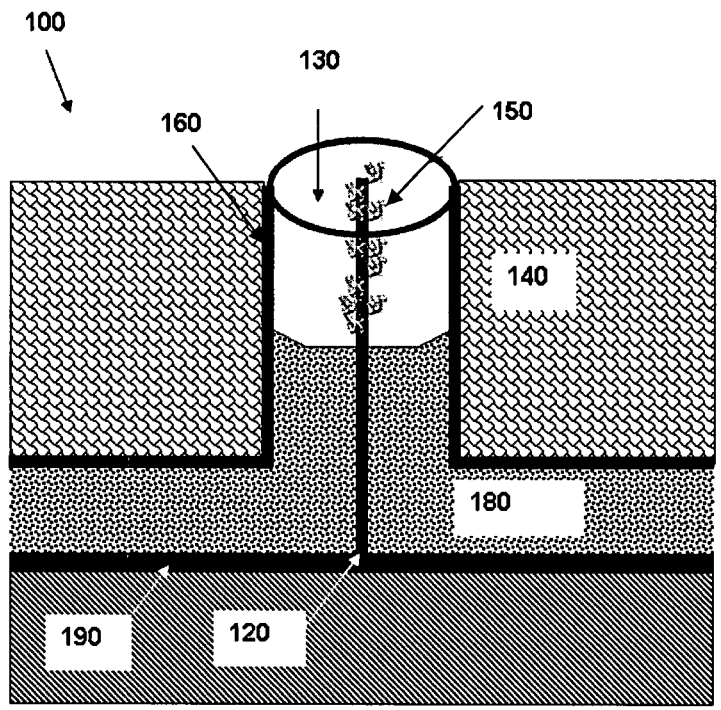

FIG. 1A

$$R = \frac{\rho}{2\pi \cdot L} \ln(D/d)$$ where $\rho$ is the resistivity of the filling in the gap.

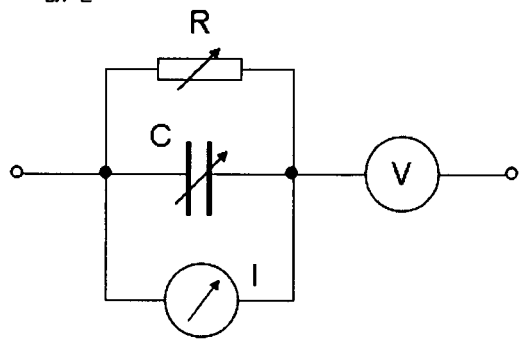

$C = 2\pi \varepsilon_o \varepsilon_r \cdot L/\ln(D/d)$ where $\varepsilon_o$ is the permittivity of free space, and $\varepsilon_r$ is the relative dielectric constant that contributed by the solution composition and biological species. $D$ is the diameter of the outer shell, and $d$ is the diameter of the carbon nanoutbe. L is the length of the nanotube.

FIG. 1B

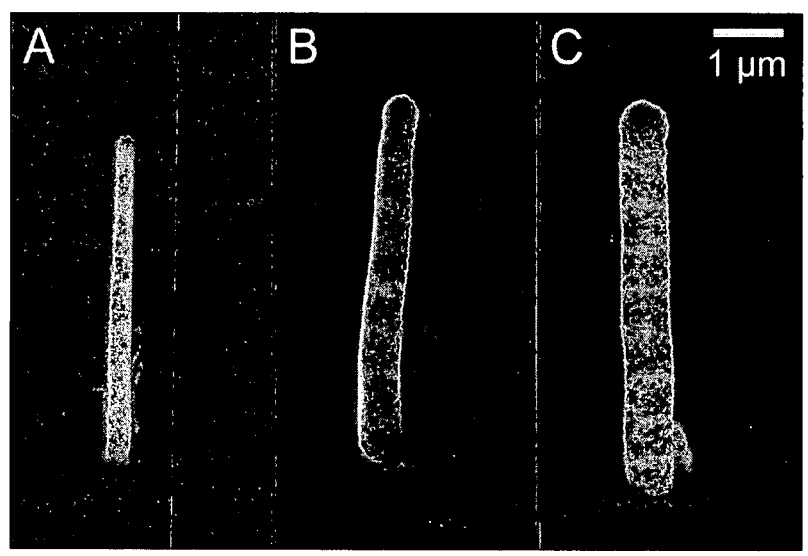
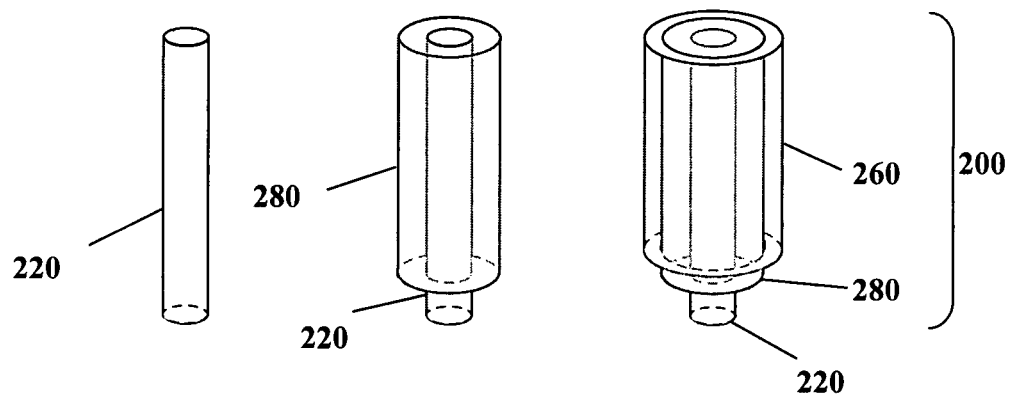
FIG. 2A     FIG. 2B     FIG. 2C

FIG. 5B  FIG. 5C

FIG. 15A   FIG. 15B   FIG. 15C   FIG. 15D
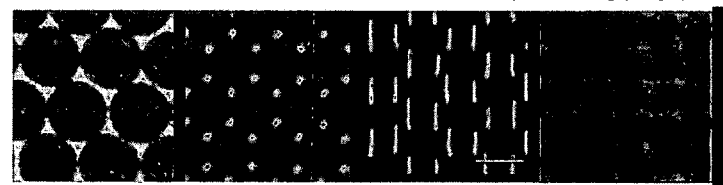
Spatial Amplification
$$V_{total} = \sum_{i=1}^{N} V_i$$
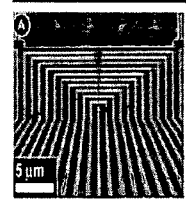
Addressing/Multiplexing
$$V = \lfloor v_{ij} \rfloor$$
for $i=1,2,...n \wedge j=1,2,...,m$
FIG. 16A   FIG. 16B   FIG. 16C   FIG. 16D
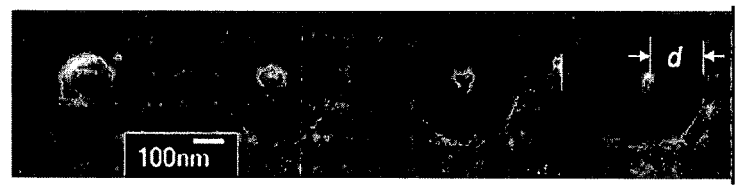
Physical selectivity
$$V = v \cdot f_{(d)}$$
$$f_{(d)} = \begin{cases} g_{(d)} & d \leq D_0 \\ 0 & d = \text{other} \end{cases}$$
FIG. 17

NANOSCALE SENSORS

CROSS-REFERENCE TO RELATED PATENT APPLICATIONS

This application is the U.S. National Stage of PCT International Application No. PCT/US2007/024043, filed Nov. 16, 2007, which claims priority from U.S. Provisional Application No. 60/859,735, filed Nov. 17, 2006, the contents of which are incorporated herein by reference in their entireties.

BACKGROUND OF THE INVENTION

The present invention relates generally to the field of nanoscale sensors, and more particularly to an apparatus and method for detecting a target species using nanoscale sensors.

Chemical and biological sensors typically operate at elevated temperatures to enhance chemical reactivity, and often require long recovery times (if recoverable at all), poor reproducibility, and are applicable to the detection of a very limited range of chemical and biological species and are described in U.S. Pat. No. 7,013,708, entitled "Carbon Nanotube Sensors"; U.S. Pat. No. 7,166,325, entitled "Carbon Nanotube Devices"; U.S. Application Publication No. 2003/0134267, entitled "Sensor for Detecting Biomolecule Using Carbon Nanotubes"; U.S. Application Publication No. 2004/0245209, entitled "Method for Fabricating a Carbon Nanotube Array and a Biochip Using the Self-Assembly of Supramolecules and Staining of Metal Compound"; U.S. Application Publication No. 2005/0181409, entitled "Biochip and Biomolecular Detection System Using the Same"; and U.S. Patent Application Publication No. 2005/0230270, entitled "Carbon Nanotube Nanoelectrode Arrays."

An article by Choi et al., entitled "YY1-DNA interaction results in a significant change of electronic context as measured by capacitance," *Biophysical Chemistry* 103, 109-115 (2003), which is incorporated herein by reference in its entirety, describes a nanosensor that detects a dielectric change upon the formation of a specific Yin-Yang 1 (YY1)-DNA complex within an 80-nm gap between two electrodes of a capacitor. Aliquots of a mixture of YY1 and P5 promoter DNA were placed on the capacitor and, after a 5-min incubation period, the capacitance was measured between 10 kHz and 3 MHz. Changes in the capacitance were attributed to the specific YY1-DNA complexation. It is believed that the dielectric effect is due to the alignment of dipoles to the electric field of the capacitor, whereby a stronger dipole results in greater capacitance. However, the sensitivity of the device suffered due to signal contributions arising from complexation and other contributions outside of the electrode gap.

SUMMARY OF THE INVENTION

One embodiment of the invention provides a nanosensor that includes a capacitor having a nanocavity between a first and second conductor of the capacitor. The nanosensor is adapted to exhibit each of a size-dependent physical selection of target species entering into the nanocavity, a selective capture of at least one of the target species within the nanocavity to at least one of the first and second conductors; and an electromagnetic shielding within the nanocavity such that a signal produced in response to the selective capture within the nanocavity is substantially undisturbed by a capture outside of the nanocavity.

Another embodiment of the invention provides a nanocoaxial sensor that includes an outer conductor, an inner conductor, a nanocavity sized to allow target species to enter the nanocavity between the outer and inner conductors, and an active sensing element immobilized within the nanocavity on at least one of the inner or outer conductors. The active sensing element is adapted to selectively capture at least one of the target species.

Another embodiment of the invention provides a method of making a nanocoaxial sensor. The method includes providing an array of vertically-aligned nanostructures grown substantially perpendicular to a substrate, wherein each nanostructure is circumferentially surrounded by a dielectric material disposed within a metal cylinder, and forming at least one nanocavity by removing at least a portion of the dielectric material located on a side of the array opposite the substrate.

Another embodiment of the invention provides a method of using a nanosensor to detect a presence of a target species. The method includes transmitting electromagnetic waves through a medium disposed between a first and second electrode of the nanosensor, wherein the first and second electrodes comprise an inter-electrode spacing of no more than about 500 nm and the waves are substantially shielded by the first and second electrodes, and monitoring for a change in the electromagnetic waves based on a change in a dielectric constant between the first and second electrodes, wherein the change in the dielectric constant corresponds to the presence of the target species between the first and second electrodes.

BRIEF DESCRIPTION OF THE DRAWINGS

FIG. 1A shows a schematic image of a nanoscale sensor unit structure according to an embodiment of the present invention.

FIG. 1B shows an equivalent circuit diagram of the nanoscale sensor unit structure of FIG. 1A.

FIG. 2A-2C show schematic and exemplary views of a nanoscale coaxial transmission line built around a carbon nanotube. FIG. 2A shows a schematic view and an exemplary view of a carbon nanotube. FIG. 2B shows a schematic view and an exemplary view of the carbon nanotube in FIG. 2A after coating with a dielectric material. FIG. 2C shows a schematic view and an exemplary view of the carbon nanotube in FIG. 2B after coating with an outer conductor material.

FIG. 5 shows a nanoscale coaxial transmission line array according to an embodiment of the present invention. FIG. 5B shows a cross-section view of a single nanoscale coaxial transmission line viewed by a scanning electron microscope. FIG. 5C shows an energy dispersive x-ray spectroscopy (EDS) analysis of the composition of the coaxial layers showing concentration mapping for silicon (Si), chromium (Cr), and aluminum (Al).

FIG. 6A shows a high-resolution optical microscope image of white light reflected from the nanoscale coaxial transmission line medium. FIG. 6B shows a high-resolution optical microscope image of white light transmitted through the medium. FIG. 6C is an SEM image of the nanoscale coaxial transmission line medium surface (tilted 45 deg). FIGS. 6A-6C have the same magnification. FIG. 6D shows an image of a laser beam with λ=532 nm transmitted through a glass substrate (exposure time 0.0025 sec). FIG. 6E shows an image of a laser beam with λ=532 nm transmitted through the nanoscale coaxial transmission line medium on the same glass substrate (exposure time 1 sec). FIG. 6F shows an image of a laser beam with λ=680 nm transmitted through a glass substrate (exposure time 0.0025 sec). FIG. 6G shows an image of a laser beam with λ=680 nm transmitted through the nanoscale coaxial transmission line medium on the same glass substrate (exposure time 1 sec). FIGS. 6D-6G have the same magnification.

FIG. 7D shows a plot of measured intensity of the transmitted light at fixed wavelength (λ=532 nm) versus sample thickness.

FIG. 15A-15D are SEM images showing the steps used to fabricate an array of nanocoaxial sensors according to an embodiment of the present invention.

FIG. 16A-16D show an individually-addressable array of nanocoaxial sensors according to an embodiment of the present invention.

FIG. 17 are SEM images showing the tunability of the size of the nanocavity openings of the nanocoaxial sensors according to an embodiment of the present invention.

FIG. 18A is a schematic diagram of an experimental setup used to nucleate a gold film. FIG. 18B is a plot of resistivity versus temperature of the gold film. FIG. 18C shows the steps of a method for functionalizing CNTs with gold nanoparticles according to an embodiment of the present invention.

Figures 3A, 3B:
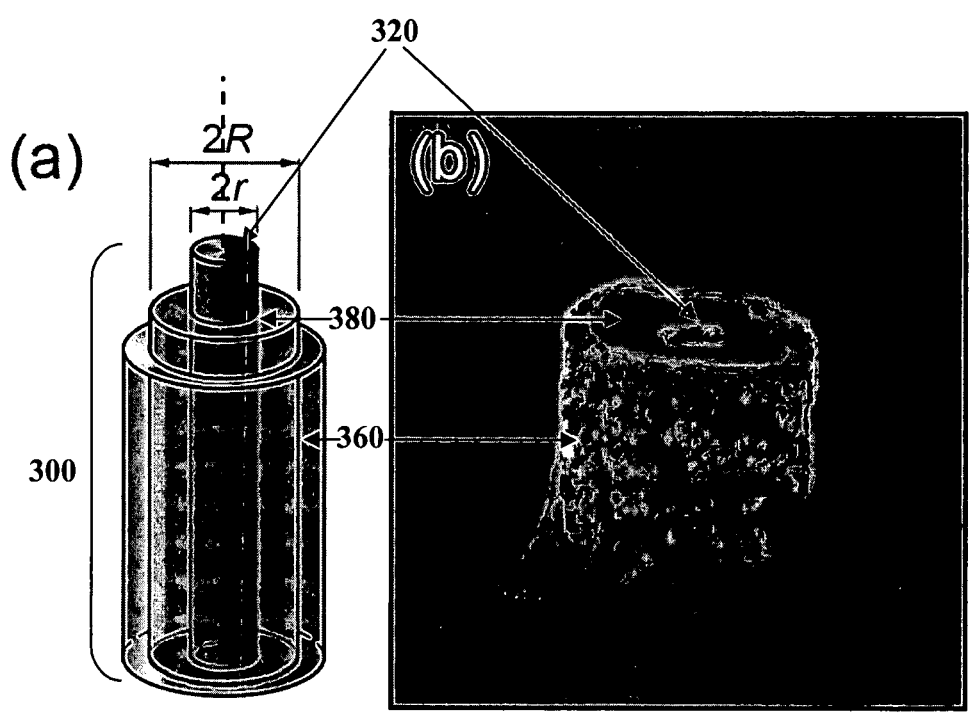
FIG. 3A shows a schematic view of a nanoscale coaxial transmission line built around a carbon nanotube.
FIG. 3B shows a scanning electron microscope (SEM) image of the nanoscale coaxial transmission line built around a carbon nanotube. The carbon nanotube's diameter is about 100 nm.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION OF THE PREFERRED EMBODIMENTS

The embodiments disclosed herein relate to the field of nanoscale sensors, and more particularly to an apparatus and method for ultrasensitive sensing of target species, such as chemical and/or biological molecules, using nanoscale sensors. Methods of fabricating a nanoscale sensor apparatus are also disclosed. The nanoscale sensors are able to capture the real-time signals from a single target species. The nanoscale sensors may be used in various biomedical related applications including, but not limited to, clinic diagnosis, bio-attack alarming system, drinking water monitoring, biomolecule characterization in research, constructing an artificial neuronal post-synaptic membrane, food quality test, allergic species detection, forensic examination, and personnel biological identification. The nanoscale sensors may be used in various non-biomedical areas including, but not limited to, explosive detection, narcotics control, and pollution monitoring.

The basic elements of nanoscale capacitance sensor measurements are disclosed. The nanoscale sensors are used to detect particles of bio-species, for example, with ultrasensitivity that affords single molecule detection. The nanoscale sensor unit structure comprises a dielectric material located between a first electrical conductor and a second electrical conductor. The nanoscale sensor unit structure constitutes a nanoscale capacitor and forms a nanoscale coaxial transmission line built around an internal conductor with the diameter registered at any value between about 1 nm and about 1000 nm, such as about 40 nm to about 200 nm, for example about 100 nm. Biomolecules, or biologically active sensing elements, are immobilized either on the first conductor or the second conductor, or both.

The following definitions are used to describe the various aspects and characteristics of the presently disclosed embodiments.

As used herein, "nanostructures" and "nanostructure materials" refer to a broad class of materials, with microstructures modulated in zero to three dimensions on length scales less than about 1,000 nm; materials with atoms arranged in nano-sized clusters, which become the constituent grains or building blocks of the material; and any material with at least one dimension in the about 1-1,000 nm range. Using a variety of synthesis methods, it is possible to produce nanostructured materials in the following forms: nanorods, nanowires, nanopillars, nanofibers, nanotubes, nanohorns, thin films, coatings, powders and as a bulk material. In an embodiment, the material comprising the nanostructure is carbon. In an embodiment, the material comprising the nanostructure need not be carbon. In applications where symmetric structures are generated, the sizes (largest dimensions) can be as large as tens of microns.

As used herein, "carbon nanotubes" and "CNTs" are used interchangeably. These terms primarily refer to a type of carbon nanofiber having cylindrical carbon molecules. CNTs may have unique properties that make them potentially useful in a wide variety of applications in nanotechnology, electronics, optics, and other fields of materials science. They exhibit extraordinary strength and unique electrical properties, and are efficient conductors of heat.

As used herein, "single-walled carbon nanotubes" (SWCNTs) are made of one graphene sheet rolled into a cylinder. "Double-walled carbon nanotubes" (DWCNTs) are made of two graphene sheets in parallel, and those with multiple sheets (typically about 3 to about 30) are "multi-walled carbon nanotubes" (MWCNTs). For the coaxial nanostructures disclosed herein, MWCNTs need not be specifically graphitic (i.e. crystalline graphene) in structure, but can be fibrous. MWCNTs are a type of carbon nanotube, and carbon nanotubes are a type of carbon nanofiber.

As used herein, a CNT is "vertically aligned" when its longitudinal axis is oriented substantially perpendicular to a substrate on which the CNT's proximal end is in contact, for example the substrate from which the CNT is grown. CNTs may be vertically aligned even if they are not exactly perpendicular to the substrate and even if they are curved or kinked.

As used herein, a "tubule" is an individual CNT.

As used herein, "linear CNTs" refer to CNTs that do not contain any branches originating from the surface of individual CNT tubules along their linear axes.

As used herein, "conductor" refers to an electrically conducting material. A conductor may be a metallic or non-metallic material.

As used herein CNTs have a "uniform length" wherein the length of individual tubules are substantially the same length relative to one another. Depending on growth conditions used, the height of a CNT in an array in a given growth run can be varied in height by about 10% to about 50%. Alternatively, height uniformity is accomplished by performing additional mechanical polish steps. In an embodiment, the CNTs have a uniform length from about 1 to about 50 micrometers.

As used herein, the "aspect ratio" of a CNT is the ratio of tubule length and tubule diameter.

The CNTs have "proximal" and "distal" ends. The proximal ends of the CNTs engage a substrate.

As used herein, a "nanoscale coaxial transmission line" refers to a nanoscale coaxial wire, which includes a plurality of concentric layers. In an embodiment, the nanoscale coaxial transmission line has three concentric layers: an internal conductor, a dielectric material around the internal conductor, and an outer conductor. Transmission of electromagnetic energy inside the coaxial line is wavelength-independent and happens in transverse electromagnetic (TEM) mode. In an embodiment, the internal conductor is a metallic core. In an embodiment, the outer conductor is a metallic shielding that increases the signal-to-noise ratio of the detected signal.

As used herein, a "nanoscale coplanar line" refers to a nanoscale coplanar structure, which includes a plurality of parallel layers. In an embodiment, the nanoscale coplanar line has three parallel layers: two metallic conductors, with a dielectric coating between them. Transmission of electromagnetic energy inside the coplanar line is wavelength-independent and happens in transverse electromagnetic (TEM) mode.

As used herein, "transverse electromagnetic (TEM)" refers to an electromagnetic mode in a transmission line for which both the electric and magnetic fields are perpendicular to the direction of propagation. Other possible modes include but are not limited to transverse electric (TE), in which only the electric field is perpendicular to the direction of propagation, and transverse magnetic (TM), in which only the magnetic field is perpendicular to the direction of propagation.

As used herein, "nano-optics" is the study of optical interactions with matter on a subwavelength scale, i.e., nanoscale optics.

As used herein, an "optical signal" refers to any electromagnetic radiation pulse including gamma rays, X-rays, ultraviolet light, visible light, infrared, microwaves, radio waves (ULF, VLF, LF, MF, HF, long, short, HAM, VHF, UHF, SHF, EHF), cosmic microwave background radiation and other forms of radiation of the electromagnetic spectrum.

As used herein, a "non-metallic material" is any non-conductive material suitable for depositing a metallic layer thereupon. Examples of "non-metallic materials" include but are not limited to, silicon, silica, glass, alumina, quartz, polymer and graphite. Examples of non-metallic polymers include but are not limited to, polyvinyl chloride (PVC), polyacrylate (PA), polypropylene (PP), polyphenol (PPN), polymethylmethacrylate (PMMA), polycarbonate (PC), polyethylene (PE) and thermoset plastics. In an embodiment, the non-metallic material is a silicon wafer.

As used herein, a "metallic material" can be a metal, metal alloy or mixture thereof. Examples of a metallic material include, but are not limited to, chromium (Cr), molybdenum (Mo), tungsten (W), ruthenium (Ru), copper (Cu), silver (Ag), gold (Au), and conductive polymers. In an embodiment, the metallic material is chromium (Cr).

As used herein, a "catalytic transition metal" can be any transition metal, transition metal alloy or mixture thereof. Examples of a catalytic transition metal include, but are not limited to, nickel (Ni), silver (Ag), gold (Au), platinum (Pt), palladium (Pd), iron (Fe), ruthenium (Ru), osmium (Os), cobalt (Co), rhodium (Rh) and iridium (Ir). In an embodiment, the catalytic transition metal comprises nickel (Ni).

As used herein, a "catalytic transition metal alloy" can be any transition metal alloy. Preferably, a catalytic transition metal alloy is a homogeneous mixture or solid solution of two or more transition metals. Examples of a catalytic transition metal alloy include, but are not limited to, a nickel/gold (Ni/Au) alloy and a cobalt/iron (Co/Fe) alloy.

In an embodiment, a working electrode is a metallic coated non-metallic substrate for use in depositing a catalytic transition metal. In an embodiment the working electrode is a chromium (Cr) coated silicon (Si) wafer. The chromium (Cr) coating provides a flat, conductive and defect free surface on the silicon (Si) wafer. A method of preparing a chromium (Cr) coated silicon (Si) wafer comprises sputtering a layer of chromium (Cr) on a silicon (Si) wafer. In an embodiment the sputtering method is magnetron sputtering.

In an embodiment, a counter electrode is any suitable electrically-conductive metal. In an embodiment, the counter electrode comprises a noble metal. Examples of suitable noble metals include, but are not limited to, gold (Au), platinum (Pt) and iridium (Ir). In an embodiment, the counter electrode is gold (Au) plate.

In an embodiment, an electrolytic solution is a transition metal salt and a mineral acid. Preferably, the transition metal salt is a transition metal sulfate. In an embodiment, the transition metal sulfate is nickel sulfate ($NiSO_4$). Examples of suitable mineral acids include but are not limited to boric acid ($H_3BO_3$), nitric acid ($HNO_3$), hydrochloric acid (HCl) and sulfuric acid ($H_2SO_4$). Preferably the electrolytic solution is weekly acidic. In an embodiment, the mineral acid is boric acid ($H_3BO_3$). For example, the electrolytic solution comprises 0.01 M nickel sulfate ($NiSO_4$) and 0.01 M boric acid ($H_3BO_3$) in double distilled water.

Pulse-Current Electrochemical Deposition (PCED) is an electrochemical deposition process which utilizes a modulated current waveform (a current pulse). PCED can be used to achieve superior leveling of the deposit, and to minimize porosity and contamination. PCED is performed by applying a constant current pulse by using a current source and a voltage source. Both the current source and the voltage source are controlled by any suitable means known in the art including analog and digital controller devices. In an embodiment, the current source and the voltage source is controlled by a computer. In an embodiment, PCED is performed by applying a constant current pulse to a two electrode system comprising a working electrode and a counter electrode. The working electrode and the counter electrode are spaced at a suitable distance. In an embodiment, PCED is carried out on a two electrode system, wherein the distance between the two electrodes is maintained at about 1 cm, and a constant current pulse is applied by using a current source and a voltage source, both of which are controlled by the computer program. The working electrode is prepared by sputtering a layer of chromium on a silicon wafer thereby obtaining a flat, conductive and defect free surface. A gold plate is used as a counter electrode. About 1 cm$^2$ of the working electrode surface is exposed to a weakly acidic electrolyte solution comprising 0.01 M NiSO$_4$ (0.01M Ni$^{2+}$) and 0.01 M H$_3$BO$_3$ in double distilled water at room temperature. PCED is performed at any suitable temperature. In an embodiment, the PCED is performed at room temperature.

Many factors with PCED can affect the deposited microparticles, including the composition of the electrolyte solution; the surface morphology of the substrate; the magnitude of the applied pulse current density and the duration time. Lowering the concentration of transition metal ions will decrease both the nucleation site density and the size of the deposited catalytic transition metal microparticles.

Varying mineral acid concentrations, such as boric acid concentrations, changes the pH value. Solutions with a support electrolyte (potassium chloride) added are tested and it is found only when the concentration of mineral acid is very low and no other support electrolyte is added, the catalytic transition metal microparticles with low site density and large size (larger than 100 nm in diameter) are achieved. When the mineral acid concentration increases or some other support electrolyte is added, the conductivity of the solution increases, and the electrodeposited catalytic transition metal microparticles have higher density and smaller size. The surface morphology of the substrate also affects the distribution of the deposited catalytic transition metal microparticles. Microparticles form on the defect site of the substrate with high site density. In order to eliminate the aggregation of the microparticles, a sputtering method is used to coat a thin layer of metallic material such as chromium (Cr) on the non-metallic substrate material such as a silicon (Si) wafer to obtain a conductive and defect free surface.

When the solution composition and the substrate are fixed, the site density and the size of the catalytic transition metal microparticles are determined by the combined effect of applied pulse current density and duration time. High current density and long duration time result in high site density and large particles (greater than about 100 nm).

In an embodiment, the size distribution of the electrochemical deposited catalytic transition metal microparticles is quite large. Both large particles (greater than about 100 nm) and small particles (less than about 50 nm) are deposited on the substrate material. The morphology of the CNTs is related to the size of the catalytic transition metal microparticles. When the diameter of the catalytic transition metal microparticles is smaller than about 50 nanometers, either no CNTs or only short and curved CNTs are grown. When the size of the catalytic transition metal microparticles is large, well-aligned CNTs with uniform length distribution are grown. In an embodiment, the substrate material is optionally plasma etched prior to CNT growth to substantially reduce the number of catalytic transition metal microparticles that have a diameter smaller than about 50 nanometers. The plasma etches the catalyst substrate and at the same time assists the CNT growth.

CNTs can be grown by any suitable method known in the art. For example, CNTs can be grown by any chemical vapor deposition (CVD) method, including but not limited to, plasma enhanced chemical vapor deposition (PECVD), hot filament chemical vapor deposition (HFCVD) or synchrotron radiation chemical vapor deposition (SRCVD). In CVD, gaseous mixtures of chemicals are dissociated at high temperature (for example, $CO_2$ into C and $O_2$). This is the "CV" part of CVD. Some of the liberated molecules may then be deposited on a nearby substrate (the "D" in CVD), with the rest pumped away. In an embodiment, CNTs are obtained by placing a catalyst substrate material, which is formed by electrochemical deposition of catalytic transition metal microparticles, with a pre-determined site density, on a metal coated non-metallic substrate material, within a PECVD chamber known in the art, following which CNT growth is initiated on the surface of the catalyst substrate material by standard methods described in the art (see for example Z. F. Ren, et al., Science, 282, 1105 (1998); Z. P. Huang, et al., Appl. Phys. A: Mater. Sci. Process, 74, 387 (2002); and Z. F. Ren et al., Appl. Phys. Lett., 75, 1086 (1999), all of which are incorporated herein by reference in their entirety).

A promoter gas can be a substance that is a gaseous compound at the reaction temperatures, and preferably comprises a non-carbon gas such as ammonia, ammonia-nitrogen, hydrogen, thiophene, or mixtures thereof. The promoter gas may be diluted by mixing it with a diluent gas, which are primarily unreactive, oxygen-free gases, such as for example, hydrogen, helium, nitrogen, argon, neon, krypton, xenon, hydrogen sulfide, or combinations thereof. For the CVD reaction process of the presently disclosed embodiments, hydrogen is preferred for reaction temperatures maintained at less than about 700° C., while for higher temperatures (greater than or equal to about 700° C.), the promoter gas is chosen from ammonia, hydrogen, nitrogen, or any combination thereof. The promoter gas can be introduced into the reaction chamber of the reaction apparatus (e.g. the CVD reaction chamber) at any stage of the reaction process. Preferably, the promoter gas is introduced into the reaction chamber either prior to or simultaneously with the carbon source gas. The CNT nanotube nucleation process on the catalyst substrate is catalyzed by the promoter gas enabling every metal catalyst "cap" that is formed within individual tubules to catalyze their efficient and rapid growth.

A carbon source gas can be saturated, unsaturated linear branched or cyclic hydrocarbons, or mixtures thereof, that are in either the gas or vapor phase at the temperatures at which they are contacted with the catalyst substrate material (reaction temperature). Preferred carbon source gases include methane, propane, acetylene, ethylene, benzene, or mixtures thereof. In an embodiment, the carbon source gas for the synthesis of linear CNTs is acetylene.

CNT tubule diameter, tubule length, number of concentric graphene layers (graphitization) comprising individual tubules and the yield of the CNTs is controlled by varying the reaction temperature of CNT synthetic process.

The manufacturing methods described herein facilitate the tailoring of linear CNT morphology by controlling gas pressure. At low pressures, CNTs with a tubular hollow structure can be obtained, whereas at high pressures, CNTs with "bamboo-like" structure and increased compartmental density can be obtained. The number of graphene layers, which is related to thickness of the tubule wall and diaphragm of the CNTs, can also be controlled during their formation by control of gas pressure. Once the first layer forms as a bamboo-like structure, all subsequent layers terminate on the surface of the CNT.

Scanning electron microscopy (SEM) is employed to examine the morphology. Transmission electron microscopy (TEM) is used to characterize the structure of the CNTs by standard methods.

A dielectric can be any a non-conducting or insulating material. Preferably, the dielectric has a low porosity, a high density and is substantially defect free. Examples of dielectrics include high-density polymers, and metal oxides. In an embodiment, the dielectric is aluminum oxide ($Al_2O_3$), $SiO_2$, MgO, $Si_3N_4$ or $TiO_2$, or a combination thereof.

As used herein, the term "ligand" or "analyte" or "marker" or "target species" refers to any molecule being detected. It is detected through its interaction with an active sensing element, which specifically or non-specifically binds the target species. The target species can be any molecule for which there exists another molecule, such as an active sensing element, which specifically or non-specifically binds to the target species, owing to recognition, chemical or otherwise, of some portion of the target species. The active sensing element, for example, can be an antibody and the target species a molecule such as an antigen which binds specifically to the antibody. In the event that the antigen is bound to the surface and the antibody is the molecule being detected, for the purposes of this document the antibody becomes the target species and the antigen is the active sensing element. The target species may include nucleic acids, proteins, lipids, small molecules, membranes, carbohydrates, polymers, cells, cell membranes, organelles and synthetic analogues thereof.

Target species include, but are not limited to, antibodies (forming an antibody/epitope complex), antigens, nucleic acids (e.g. natural or synthetic DNA, RNA, gDNA, cDNA, mRNA, tRNA, etc.), lectins, sugars (e.g. forming a lectin/sugar complex), glycoproteins, receptors and their cognate target species (e.g. growth factors and their associated receptors, cytokines and their associated receptors, signaling receptors, etc.), small molecules such as drug candidates (either from natural products or synthetic analogues developed and stored in combinatorial libraries), metabolites, drugs of abuse and their metabolic by-products, co-factors such as vitamins and other naturally occurring and synthetic compounds, oxygen and other gases found in physiologic fluids, cells, cellular constituents cell membranes and associated structures, natural or synthetic toxins, pathogens (e.g., *Bacillus anthracis, Yersinia pestis, Francisella tularensis, Coxiella burnetii*) other natural products found in plant and animal sources, other partially or completely synthetic products, pathogens (e.g. virus and bacteria, etc.), and the like. Target species may be found in a variety of heterogeneous test samples (e.g., water, saliva, sweat, urine, serum, blood, plasma, tissues and food).

The active sensing element is adapted to selectively capture at least one target species. For example, the active sensing element can specifically or nonspecifically bind with another molecule (such as a target species). Also, the active sensing element can exert specific enzymatic activity with the target species to produce intermediate molecules that can change the physiochemical environment in the nanocavity. As used herein, the active sensing element is usually immobilized on the surface of a nanoscale sensor, either alone or as a member of a binding pair that is immobilized on the surface. In some embodiments, the active sensing element may include the molecules on the signal path, on a dielectric surface or in a dielectric volume, or a conductive surface, such as on the inner or outer conductor of the coaxial nanosensor. Immobilization of the active sensing element can be performed by one or more linkers.

The selective capture of the target species can be a specific binding, such as by a binding reaction which is determinative of the cognate target species of interest in a heterogeneous population of proteins and/or other biologics. Thus, under designated conditions, the specified target species binds to its particular active sensing element (e.g., a hormone specifically binds to its receptor, or a given nucleic acid sequence binds to its complementary sequence) and does not bind in a significant amount to other molecules present in the sample or to other molecules to which the target species or antibody may come in contact in an organism or in a sample derived from an organism.

FIG. 1A shows a schematic view of a nanoscale sensor unit structure 100. The nanoscale sensor unit structure 100 comprises a dielectric material 180 located between a first electrical conductor 120 and a second electrical conductor 160. The first electrical conductor 120 serves as an internal electrode and the second electrical conductor 160 serves as an outer electrode. The nanoscale sensor unit structure 100 is supported by a metallized substrate 190, such as an insulating or semiconducting substrate that is partially or entirely coated with a metal layer. Other substrates, including substrates without a metal layer, may be used. The standing nanoscale sensor unit structure 100 is supported by a thick dielectric material 140. A nanocavity 130 is fabricated at the upper end of the nanoscale sensor unit structure 100 after chemical etching of at least a portion of the dielectric material 180. In an embodiment, the dielectric material 180 is entirely removed by etching. Alternatively, a portion of the dielectric material 180 is removed by etching. In an embodiment, the dielectric material is $Al_2O_3$ and is etched with NaOH. Active sensing elements 150 can be immobilized within the nanocavity 130, for example on the first electrical conductor 120 for selective capture of the target species. The nanocavity area houses a solution containing the target species. In an embodiment, the solution may be aqueous based, such as pure water, water with bio-molecules, physiological saline or other solutions known in the art. In an embodiment, the solution may be in organic solvents, such as acetic acid, acetone, benzene, carbon tetrachloride, chloroform, dichloromethane, dimethylformalmide (DMF), dimethylsulphonate (DMSO), ethanol, ether, ethyl acetate, light petroleum, methylated spirits (~2% methanol in ethanol), methanol, petroleum spirit, pyridine, mineral oil, or other solvents known to those skilled in the art.

The internal electrode 120 may be a nanostructure having a conductive core. Examples of materials that can be used for the internal electrode 120 include but are not limited to, carbon fiber; carbon nanotube; pure transition metals such as nickel (Ni), aluminum (Al), or chromium (Cr); metal alloys, e.g. stainless steel (Fe/C/Cr/Ni) or aluminum alloys (Al/Mn/Zn); and metallic polymers. Other internal electrodes 120 are highly doped semiconductors, and semi-metals (metals with vanishingly small band gap, e.g. graphite). In an embodiment, the internal electrode 120 is a carbon nanofiber, such as carbon nanotube, for example a SWCNT or MWCNT. The nanotubes may, but need not, be substantially of the metallic chirality. The nanotubes can include a mixture of metallic and semiconducting chiralities. The nanotubes are preferably sufficiently conductive to be used as the inner conductor of a nanocoaxial capacitor. Those skilled in the art will recognize that the internal electrode 120 may be other conducting materials known in the art and be within the spirit and scope of the present embodiments.

The dielectric material 180 circumferentially surrounds a portion of the internal electrode 120, either uniformly surrounding the internal electrode 120 or non-uniformly surrounding the internal electrode 120. In an embodiment, the dielectric material 180 may be $Al_2O_3$, $SiO_2$, MgO, $Si_3N_4$ $TiO_2$, or a non-conductive polymer, or a combination thereof, and may be deposited by sputter coating, atomic layer deposition, or electropolymerization. The dielectric material 180 can be crystalline (periodic arrangement of atoms in macroscopic scale), polycrystalline (periodic arrangement of atoms in microscopic scale), or amorphous (aperiodic arrangement of atoms in macroscopic scale). Optionally, the dielectric material 180 can be omitted.

The second electrical conductor or outer electrode 160 may be a metal nanostructure. Thus, the outer electrode 160 may take the form of a metallic cylinder. In an embodiment, the metallic cylinder provides shielding of electromagnetic waves that are transmitted along the length of the unit structure 100. Examples of outer electrodes include but are not limited to, pure transition metals such as nickel (Ni), aluminum (Al), chromium (Cr), titanium (Ti), gold (Au), platinum (Pt); metal alloys e.g. stainless steel (Fe/C/Cr/Ni) or aluminum alloys (Al/Mn/Zn); a conductive metal oxide; and metallic polymers. In an embodiment the outer electrode 160 is chromium. Those skilled in the art will recognize that the outer electrode 160 may be other conducting materials known in the art and be within the spirit and scope of the presently disclosed embodiments.

The nanoscale sensor unit structure 100 can be simplified as a nanoscale coaxial capacitor, whose capacitance is proportional to the dielectric constant of the materials filling in the gap between the internal electrode 120 and the outer electrode 160. Any method that is based on capacitance measurement is applicable to form a biosensing system with the proposed nanoscale sensor unit structure 100. The dimension of the nanoscale sensor unit structure 100 is in the nano or sub-micro range, therefore most of the target species can produce signals upon the specific binding to their active sensing elements 150 immobilized on the internal electrodes 120. Preferably, the volume of the nanocavity 130 is sufficiently small to allow magnification of the signal transduction. The signal-to-noise ratio is improved due to electromagnetic shielding between the first and second conductors 120, 160. For example, even a single molecule can be detected.

An example of an equivalent circuit of the nanoscale sensor unit structure 100 is illustrated in FIG. 1B. A method for detecting the presence of target species is any measurement method that measures the real and/or imaginary component(s) of capacitance, such as Impedance Spectroscopy (IS) and Time Domain Dielectric Spectroscopy (TDDS), by scanning over the frequency range of about 1 Hz to about 10 GHz, such as about 1 Hz to about 10 MHz or about 1 MHz to about 10 GHz, to measure the impedance and/or dielectric constant between the two conductors. For example, the presence of a target species between the two conductors induces a change in the capacitance, as manifested by a change in impedance and/or dielectric constant being measured. The present embodiments makes use of the observation that a vast number of molecules can be distinguished based upon the unique dielectric properties most molecules exhibit. These distinguishing dielectric properties can be observed by coupling an electromagnetic signal to the captured target species. The unique dielectric properties change the signal, giving it a unique signal response. The unique signal response can then be used to detect and identify the target species and other molecules which make up the molecular binding region. C, the capacitance of the nanoscale sensor unit structure 100, is variable to the change in $\in_r$ corresponding to any target species binding on the internal electrode 120. The capacitance is also sensitive to the interference of electrode-solution interface by the molecular interactions. R, the resistance between the inner electrode 120 and the outer electrode 160, is sensitive to ρ which is determined by the composition of the dielectric material 180. An electron transfer resistance exists due to electron transfer at the electrode-solution interface. If a redox couple is in the solution containing the target species, a diffusion impedance should be taken into account. These parameters are all subject to change upon the molecular bindings. V and I are electric biases (i.e., voltage and current) introduced by reactive species due to their redox properties.

IS measures the dielectric properties of a medium as a function of frequency. IS is based on the interaction of an external field with the electric dipole moment of the sample, often expressed by permittivity. This is an established method that is sensitive to polarization interfaces and intermolecular interactions, such as dipole-dipole interactions and cooperative processes, and has been used for extracting with high accuracy the electrical dipole moment for biomolecules, such as myoglobin, hemoglobin, DNA, etc. Traditionally, the recording is done with a standard time domain reflectometer. But problems associated with such a setup are the high level of drift and instabilities during generation of the signal and its detection in the sampler are usually inherent in the serial reflectometry equipment, since the registration of incident $V_o(t)$ and reflected R(t) signals is accomplished by the accumulation of several measurements. The nanoscale sensor unit structure 100 enhances the signal-to-noise ratio without such troublesome accumulation. The system performance can be further enhanced by using digital sampling oscilloscopes and automated, high-precision TDDS hardware.

FIG. 2A-2C each show a schematic view (bottom) and an exemplary view (top) of a nanoscale coaxial transmission line 200 built around a carbon nanotube 220. The schematic views show the major steps for fabricating a nanoscale coaxial transmission line 200. The exemplary views were taken using a scanning electron microscope (SEM) at a 30 degree angle relative to the sample surface.

FIG. 2A shows a schematic view and an exemplary view of a carbon nanotube as the internal electrode 220. The plasma-enhanced chemical vapor deposition (PECVD) method is used to grow vertically-aligned, multiwalled, straight carbon nanotubes with an average length of about 5-6 μm using a nickel catalyst (FIG. 2A). The catalyst is electrodeposited on a thin chromium layer (about 10 nm) sputtered on the top of a substrate.

FIG. 2B shows a schematic view and an exemplary view of a carbon nanotube 220 after coating with a dielectric material 280. The nanotube 220 was coated with a dielectric material 280 of aluminum oxide ($Al_2O_3$). The dielectric material 280 has a thickness between about 100 nm to about 150 nm or thicker.

FIG. 2C shows a schematic view and an exemplary view of a carbon nanotube 220 after being coated with a dielectric material 280 and an outer conductive material 260. The nanotube 220 coated with the dielectric material 280 was sputtered with about 100 nm to about 150 nm thick chromium layer as the outer conductor 260. In an embodiment, the outer conductor 260 is thicker than about 150 nm.

FIG. 3A-3B show a nanoscale coaxial transmission line according to an embodiment of the present invention. The nanoscale coaxial transmission lines can propagate light over large distances (>>wavelength λ) through nanostructures with nanoscopically restricted, subwavelength transverse dimensions (<<λ). A schematic of a nanoscale coaxial transmission line 300 is illustrated in FIG. 3A. The nanoscale coaxial transmission line 300 (with a center located at the dashed line) includes a metallic nanostructure wire 320 of radius r, a dielectric filling material with radius R, and a coaxial metallic cylinder 360 with inner radius R. A dielectric medium 380 fills the gap in between the wire 320 and the cylinder 360. The physics of the conventional coaxial cable is well-established: (i) the basic transmitted mode is transverse electromagnetic (TEM), (ii) for this mode, the wave impedance of the coaxial cable is identical to that of free space filled with the same dielectric medium as in the coaxial cable (iii) this mode operates at arbitrary frequency (i.e. no cut-off), and (iv) attenuation is dominated by resistive losses in the metal.

In conventional coaxial cable theory, the assumption is that the electrode metals are nearly perfect, i.e. highly conductive, and the dielectric medium between electrodes is of very low loss. Impedance matching of a coaxial cable to free space can be achieved very efficiently by extending the center conductor beyond the coax end, so that it forms an antenna. The nanoscale coaxial transmission line 300 retains approximately all of the above properties of the conventional coaxial cables.

In the visible frequency range, conventional coaxial cable theory must be modified because of plasma effects. Typically, metals have their plasmon resonances (bulk and surface) in the visible or UV frequency ranges. Interaction of the plasmon resonances with transmission line modes (photon modes) leads to new modes, so-called plasmon polaritons. Each metal-dielectric interface in a nanoscale coaxial transmission line of the presently disclosed embodiments supports a plasmon polariton. Consider a single, planar interface between a metal with dielectric function $\epsilon_1$ and a uniform dielectric with dielectric constant $\epsilon_2$. Solving this problem involves matching plane wave solutions of Maxwell's equations in each region across the interface, using standard boundary conditions. To describe the metallic region, the Drude dielectric function $\epsilon_1 = \epsilon_b - \omega_p^2/(\omega^2/(i\omega\gamma))$, can be used, where $\omega$ is the frequency, $\omega_p$ is the metal's plasma frequency, $\gamma$ is the damping parameter, and $\epsilon_b$ is the contribution from bound electrons in the metal.

Figure 4:
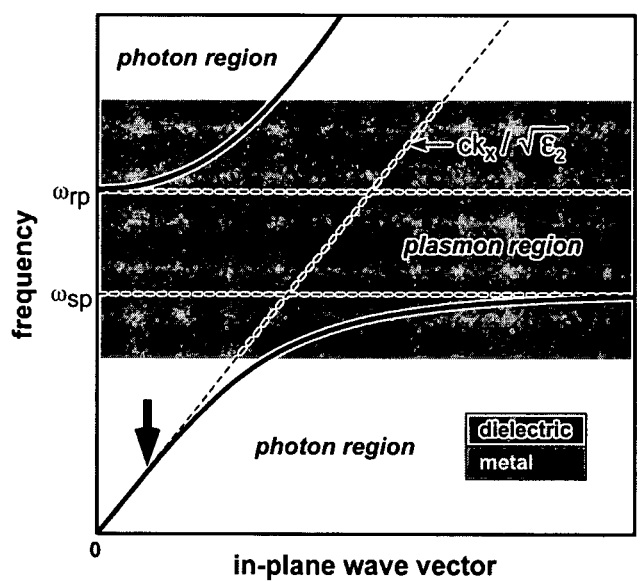
FIG. 4 shows the plasmon polariton dispersion $\omega(k)$ at the metal-dielectric interface of a nanoscale coaxial transmission line according to an embodiment of the present invention.

FIG. 4 shows a plot of frequency as a function of in-plane wave vector. The resulting eigenmode of the system, the plasmon polariton, has the dispersion (for $\gamma \to 0$). The topology and meaning of this dispersion relation is clear: the "light line" ($\omega = ck_x/\sqrt{\epsilon_2}$) crosses the surface ($\omega_{sp} = \omega_p/\sqrt{\epsilon_2 + \epsilon_b}$) and bulk ($\omega_{rp} = \omega_p/\sqrt{\epsilon_b}$) plasmon resonances, and this anti-crossing results in the two-branch structure of the plasmon polariton. For small values of $k_x$, the lower branch asymptotically approaches the light line (arrow in FIG. 4), so that the plasmon polariton becomes identical to the free-space TEM photon mode. In the higher, plasma frequency range, on the other hand, there is a drastic departure from the simple free-space plane wave behavior: a gap opens in the spectrum, and the plasmon polariton acquires "mass" at the renormalized bulk plasmon frequency ($\partial^2\omega/\partial k_x^2 \neq 0$).

Elements of this mode structure prevail in the nanoscale coaxial transmission line 300. The main conclusions regarding the low-frequency solution ($\omega \ll \omega_p$), however, are essentially the same as above, as long as (a) $d = R - r \geq \delta_0$, where $\delta_0 = \sqrt{2/\omega\sigma\mu_0}$ is the penetration depth into the metal, $\sigma$ is the dc-conductivity of the metal, and (b) $2r > d_c = c/\omega_p$. Then, the plasmon polariton in the nanoscale coaxial transmission lines of the presently disclosed embodiments has dispersion given by $$k_x = (\omega/c)\sqrt{\epsilon_2} - i\alpha \tag{1}$$

where $$\alpha = F(\omega, \gamma)\frac{\sqrt{\epsilon_2}}{\ln(R/r)}\left(\frac{1}{r} + \frac{1}{R}\right) \ll Re(k_x) \tag{2}$$

This shows that the transmitted mode is again essentially free-space TEM (because of the linear dispersion and the fact that $k_z = \sqrt{(\omega/c)^2\epsilon_2 - k_x^2} \approx 0$) and it is propagating along the coaxial transmission line 300 in the x direction, outside the inner nanostructure conductor 320 (the wave vector depends only on $\epsilon_2$). The exponential decay along the propagation direction (due to losses in the metal) is parameterized by $\alpha$, or alternatively by the photon propagation length $L = 1/\alpha$. In the extreme low frequency limit, $\omega \ll \gamma \ll \omega_p$, $F(\omega,\gamma) \approx \sqrt{\omega\gamma}/2$ $\sqrt{2}\omega_p = (2\sigma\delta_0)^{-1}$ and Equation (2) reduces to the well-know decay constant of a conventional coaxial cable mode. In the intermediate frequency range, $\gamma \ll \omega \ll \omega_p$, the difference is that the mode experiences much slower decay described by Equation (2), with $F(\omega,\gamma) \approx \gamma/4\omega_p$.

The nanoscale coaxial transmission line 300 shown in FIGS. 3A and 3B are based on a multi-walled carbon nanotube used as the inner nanostructure conductor 320. Carbon nanotubes are substantially conductive, with plasma frequency ($\omega_P$) at about 6 eV, and losses in the visible range comparable to those in Cu, i.e. $\approx 0.003\omega_p$. For the carbon nanotubes 320 shown in FIGS. 3A and 3B, r is about 50 nm, and thus $2r > d_c = c/\omega_p \approx 50$ nm. The diameter of the inner conductor 320 can range from about 40 nm to about 200 nm, such as about 80 nm to about 150 nm. For the nanoscale coaxial transmission line 300 shown in FIGS. 3A and 3B, aluminum oxide ($Al_2O_3$, $\epsilon_2 = 2.62$ in the visible range) may be used as the transparent dielectric material 380. The thickness (d) of the dielectric 380 is about 100 nm, which assures that the nanoscale coaxial transmission line 300 shown in FIGS. 3A and 3B is a subwavelength transmission line, and also that $d = 100$ nm $\gg \delta_0 \sim 10$ nm. The thickness of the dielectric 380 can range from about 10 nm to about 500 nm, such as about 50 nm to about 300 nm. In an embodiment, Cr is chosen as the material for the outer electrode 360 of the nanoscale coaxial transmission line 300, whose dielectric constant in the visible range is $\epsilon_{Cr} = -3 + i18$, thus well-simulating, in the visible, the low-frequency dielectric response of a good metal. The nanoscale coaxial transmission line 300 propagates a weakly dispersive mode, resembling in all respects the conventional TEM coaxial cable mode in the visible frequency range. The propagation length (L) of visible light along the nanoscale coaxial transmission line 300 is about 50 μm in the visible range (i.e. about $10^2$ wavelengths), which is a suitable propagation distance for many nanoscale applications.

Figure 5A:
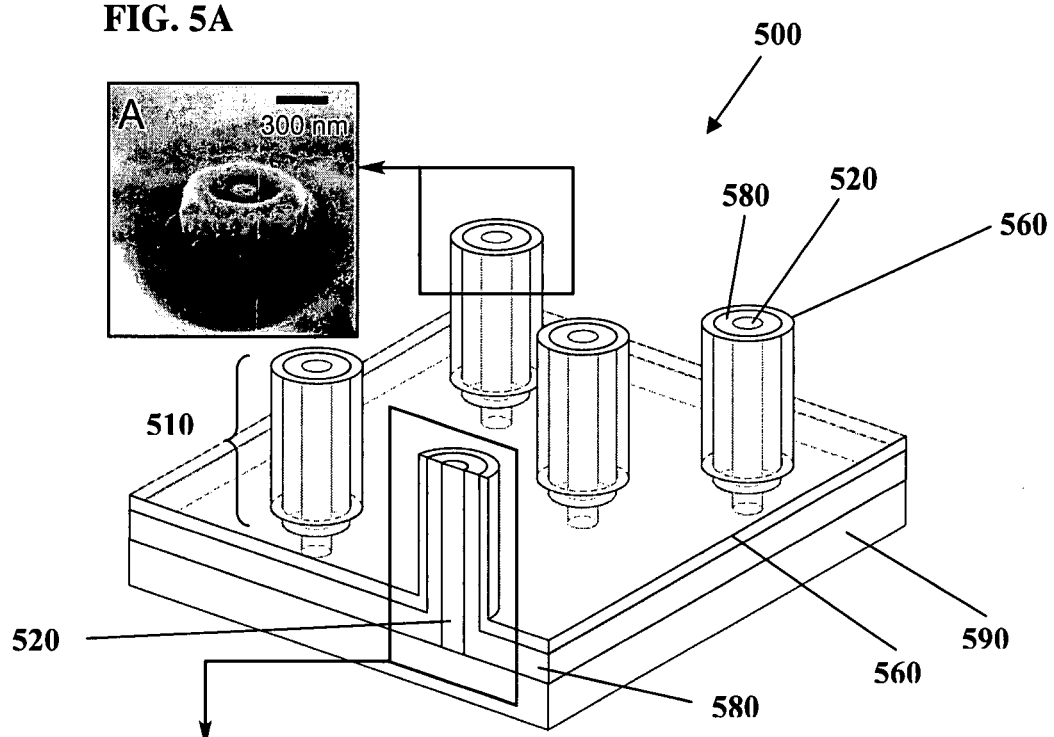
FIG. 5A shows a single nanoscale coaxial transmission line viewed by SEM.

FIG. 5 shows an apparatus 500 that is capable of transmitting visible light through nanoscale coaxial transmission lines 510 that are many wavelengths in length, with an inter-electrode separation much less than a wavelength, for example about 500 nm or less, such as about 300 nm or less. The apparatus 500 comprises the array of nanoscale coaxial transmission lines 510 distributed uniformly or periodically on a metallized substrate 590. The array of nanoscale coaxial transmission lines 510 may be aligned in rows or unevenly distributed on the metallized substrate 590. The array may be arranged in an ordered pattern on the metallized substrate 590, such as in a hexagonal pattern. The metallized substrate 590 may be transparent. The metallized substrate 590 may be composed of a polymer, glass, ceramic material, carbon fiber, glass fiber or combinations thereof onto which a layer of metallic material is deposited. The metallized substrate 590 includes a metal layer that covers a portion or all of the substrate. Optionally, the metal layer is absent and the metallized substrate 590 is not metallized. Those skilled in the art will recognize that the substrate may be other materials known in the art and be within the spirit and scope of the presently disclosed embodiments.

An array of vertically aligned conductors 520 (e.g., multi-walled carbon nanotubes or other types of nanowires or nanofibers) are grown or attached to the substrate 590. Next, the conductors 520 are coated with appropriate dielectric material 580. The conductors 520 are then coated with a metallic layer 560 acting as the outer conductor.

The apparatus 500 includes vertically aligned carbon nanotubes 520 grown on a glass substrate coated with a thin (about 10 nm) chromium layer. On this layer, nickel catalyst for PECVD growth of nanotubes was deposited electrochemically. Then, nanotubes 520 were coated with about 150 nm of aluminum oxide as the dielectric material 580 and then with about 100 nm of chromium as the metallic layer 560. The entire array of nanoscale sensor unit structures was filled with spin-on-glass (SOG) which does not affect array functionality but allowed the top part of the nanoscale coaxial transmission lines 510 to be mechanically polished off. In an embodiment, the thickness of the SOG is about 6 μm, preferably less than about 50 μm, such as less than 20 μm. Optionally, a nanocavity is etched into the dielectric material 580 and an active sensing element is immobilized within the nanocavity on the inner conductor 520 or the outer conductor 560, or both.

FIG. 5B shows a cross-section view of a single nanoscale coaxial transmission line 510 viewed by a scanning electron microscope showing the internal structure of the nanoscale coaxial transmission line 510.

FIG. 5C shows an energy dispersive x-ray spectroscopy (EDS) analysis of the composition of the coaxial layers of each of the nanoscale coaxial transmission lines 510 showing concentration mapping for spin-on-glass (SOG), chromium (Cr), and aluminum (Al). The dotted line in FIG. 5C corresponds to the position of the EDS linescan while three presented plots correspond to spin-on-glass (SOG), chromium (Cr), and aluminum (Al) concentration along the scanned line. FIG. 5C shows that the concentration of silicon is highest in the spin-on-glass (SOG) rich area. Similarly, the highest chromium concentration is present in the region of outer metallic coating of walls, and highest aluminum concentration is observed in the area of dielectric material 580 ($Al_2O_3$).

Due to the presence of the non-transparent Cr coating 560, light may pass through the sample only via the interior of the nanoscale coaxial transmission lines 510, i.e. through the inter-electrode spacing (d=R−r∼100 nm) filled with alumina. In the embodiment shown in FIG. 5, the inner electrodes 520 of each nanoscale coaxial transmission line protrudes about 250 nm on the substrate side, and thus serve as nanoantennas providing efficient coupling to external radiation. On the polished side, however, there is no antenna section, and thus, the overall transmission through a nanoscale coaxial transmission line 510 is "bottlenecked" by this antenna-less end, and is expected to be very small.

Figure 6:
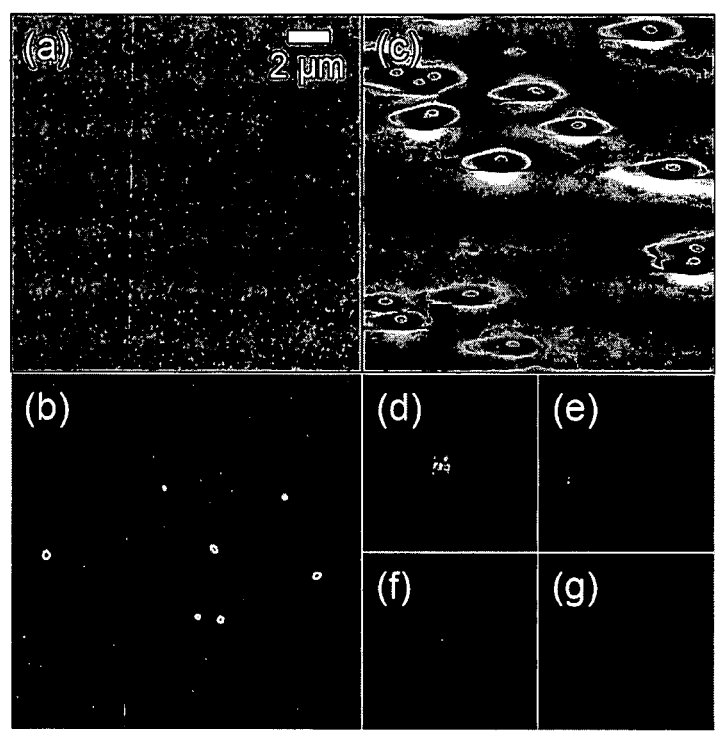
FIG. 6A-6G show the results of a small-area reflection and transmission experiment of a nanoscale coaxial transmission line according to an embodiment of the present invention.

FIG. 6A-6B show results of optical reflection and transmission from and through the apparatus 500 of FIG. 5. In the high resolution optical microscope image of FIG. 6A, white light is reflected from the top surface of the sample, showing the topography, with dark spots due primarily to absorption of light by the transmission lines 510. When the light is incident from the back-side (i.e. that with the antennae), the light is transmitted along the transmission lines 510 and emerges at the top surface, as seen by the white spots in FIG. 6B for the same region of this sample. The SEM image in FIG. 6C shows the top surface of another area of the sample at the same magnification (tilted view). The transmitted light remains white, FIG. 6B, which suggests no cut-off frequency, which is in agreement with transmission results for a larger area of this sample. FIGS. 6D and 6F show images of green and red laser beams passing directly through the glass substrate, and projected onto a screen. FIGS. 6E and 6G show the corresponding images for the laser beams transmitted through the apparatus 500. The relative intensity of the transmitted light, in each case, was obtained from RGB histograms. The overall transmission coefficient (T) for the apparatus 500 is about $10^{-3}$, in the visible range. While this value is small, it is within the expected range, given the absence of a nanoantenna on one side of each transmission line 510. Transmission (either for an array 500 or a single transmission line 510) increases with λ, and thus there is no cut-off frequency in this range, again as expected for a coaxial transmission line. The dependence of T on the transmission line 510 length has been measured, by polishing the sample to various sample thicknesses. Transmission from a large area of the sample (at λ=532 nm) is obtained as before from a RGB histogram at each polishing stage (i.e., for sample thickness of 6.2, 3.5, and 0.5 μm).

Figure 7:
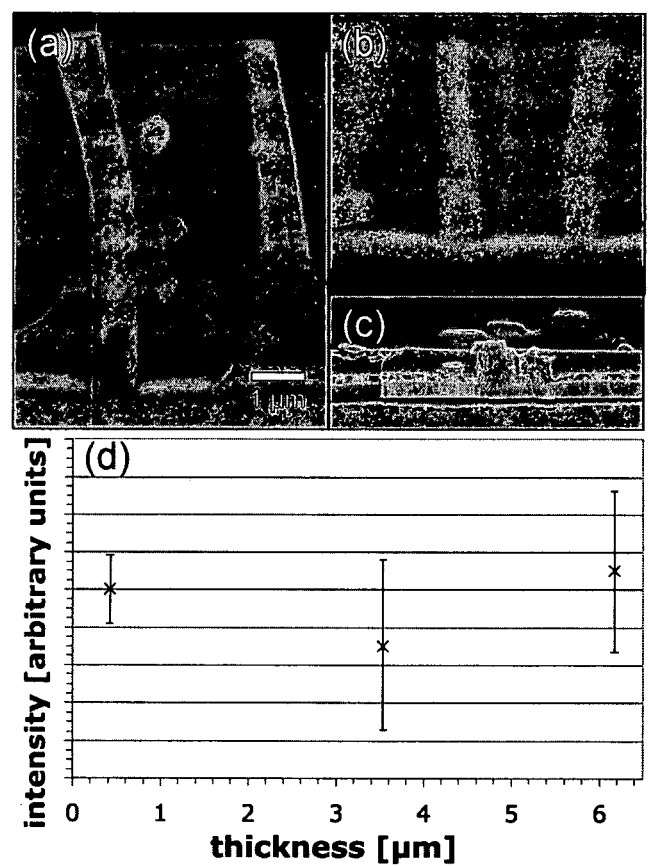
FIG. 7 shows SEM images of the cross-section of the nanoscale coaxial transmission line medium at different transmission line lengths: 6 (FIG. 7A), 3.5 μm (FIG. 7B), and 0.4 μm (FIG. 7C).

FIGS. 7A-7C show SEM images of the polished edge of the transmission lines 510 medium, with nanocoaxes clearly visible. The scales are the same in all figures. FIG. 7D is a plot of intensity versus sample thickness and shows that T is essentially independent of thickness (i.e., the transmission line 510 length). This is consistent with the theoretical value of L being about 50 μm as stated above, which is much greater than the film thickness at each stage of polishing.

The nanoscale coaxial transmission lines 500, in addition to being a subwavelength transmission line having applications in nano-optics, also facilitates many novel approaches by enabling subwavelength, nanoscale manipulation of visible light. By replacing the inter-electrode dielectric material with a nonlinear material in each nanoscale coaxial transmission line, one may achieve light mixing, switching or phase conjugation. The nanoscale coaxial transmission line medium processes the transmitted light in a discrete manner by breaking the incoming wave into wavelets, and then re-assembling the plane wave on the other side of the medium. Having control over the transmission through individual nanoscale coaxial transmission lines enables control over the re-assembled outgoing waves, which may be the basis for a new discrete optics. The nanoscale coaxial transmission line structures described herein can be fabricated from a wide variety of materials. The inner and outer conductors can be made from any appropriate metal, using soft (e.g. templated electrodeposition, CVD) or hard (electron or focused ion beam lithography) techniques, and the choice of dielectrics is extensive. Moreover, the coupling of radiation (light) to the nanoscale coaxial transmission line can be achieved in ways other than the linear antenna described herein. For example, rather than coupling the inner conductor on the substrate side, coupling can be achieved on the opposite end of the coaxial transmission line (i.e., on the distal end of the inner conductor), such as by extending the distal end of the inner conductor beyond the distal end of the inner conductor.

Figure 8A:
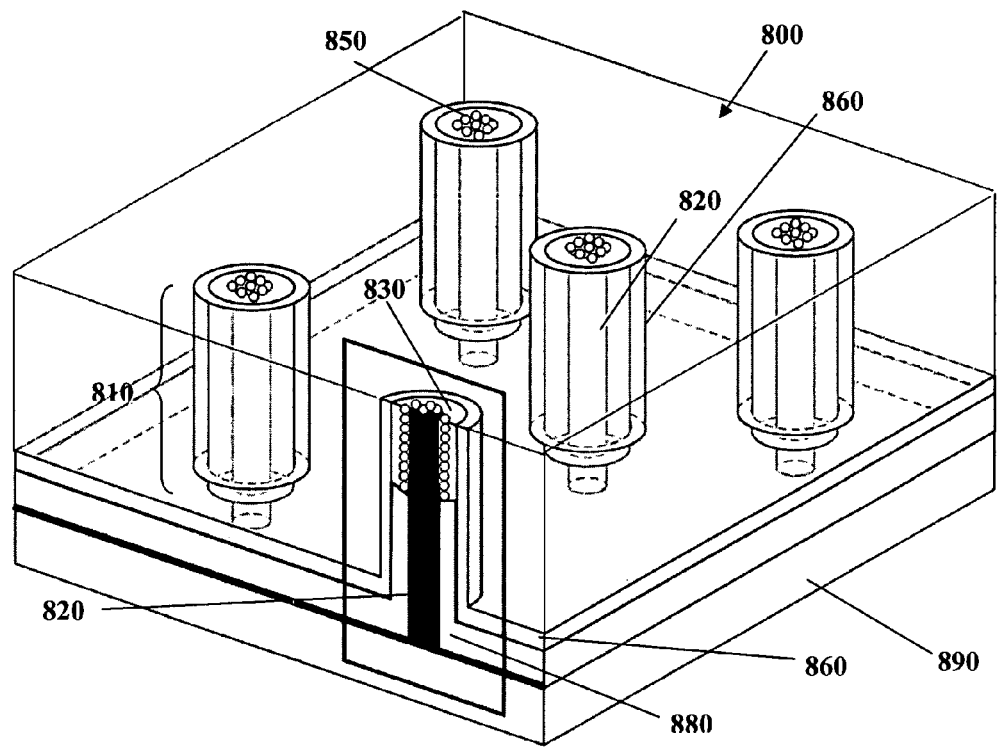
FIG. 8A-8B show a nanocoaxial sensors according to an embodiment of the present invention.

FIG. 8 shows a nanoscale sensor array 800 according to one embodiment of the present invention. The nanoscale sensor array 800 comprises an array of nanoscale sensor unit structures 810 distributed on a metallized substrate 890. The array of nanoscale sensor unit structures 810 may be arranged in a uniform, periodic or random distribution on the substrate 890. For example, the structures 810 may be arranged in a hexagonal pattern on the substrate 890. The array of nanoscale sensor unit structures 810 may be aligned in rows or unevenly distributed on the metallized substrate 890. The metallized substrate 890 may be transparent. The metallized substrate 890 may be composed of a polymer, glass, ceramic material, carbon fiber, glass fiber or combinations thereof onto which a layer of metallic material is deposited. Those skilled in the art will recognize that the substrate may be other materials known in the art and be within the spirit and scope of the presently disclosed embodiments.

An array of vertically aligned conductors 820 (e.g., multi-walled carbon nanotubes or other types of nanowires or nanofibers) are grown or attached to the substrate 890. The conductors 820 are coated with a dielectric material 880. The conductors 820 are then coated with a metallic layer 860 acting as the outer conductor.

The nanoscale sensor apparatus 800 includes vertically aligned carbon nanotubes 820 grown on a glass substrate coated with a thin (about 10 nm) chromium layer. On this layer nickel catalyst for PECVD growth of nanotubes was deposited electrochemically. The nanotubes 820 were coated with about 150 nm of aluminum oxide as the dielectric material 880 and with about 100 nm of chromium as the metallic layer 860. The entire array of nanoscale sensor unit structures 810 was filled with spin-on-glass (SOG) which does not affect array functionality but allowed the top part of the nanoscale sensor unit structures to be mechanically polished off. In an embodiment, the thickness of the SOG is about 6 μm. The nanotube 820 in each sensor unit structure 810 has the same length, unifying the array surface. Consequently, the capacitance of every nanoscale sensor unit structure 810 will be close to the same. Nanocavities 830 are formed by chemically etching at least a portion of the intermediate dielectric layer 880 between the electrodes 820 and 860. A nanocavity is opened for every nanoscale sensor unit structure 810. The nanocavity 830 is adapted to capture target species. Significant impedance change will be produced corresponding to the molecular accumulation in the nanocavity 830. A complete nanoscale sensing unit structure 810 is finished upon the addition of sensing elements 850 onto nanotubes 820. These sensing elements 850 provide specific recognition of the target species.

Figure 8B:
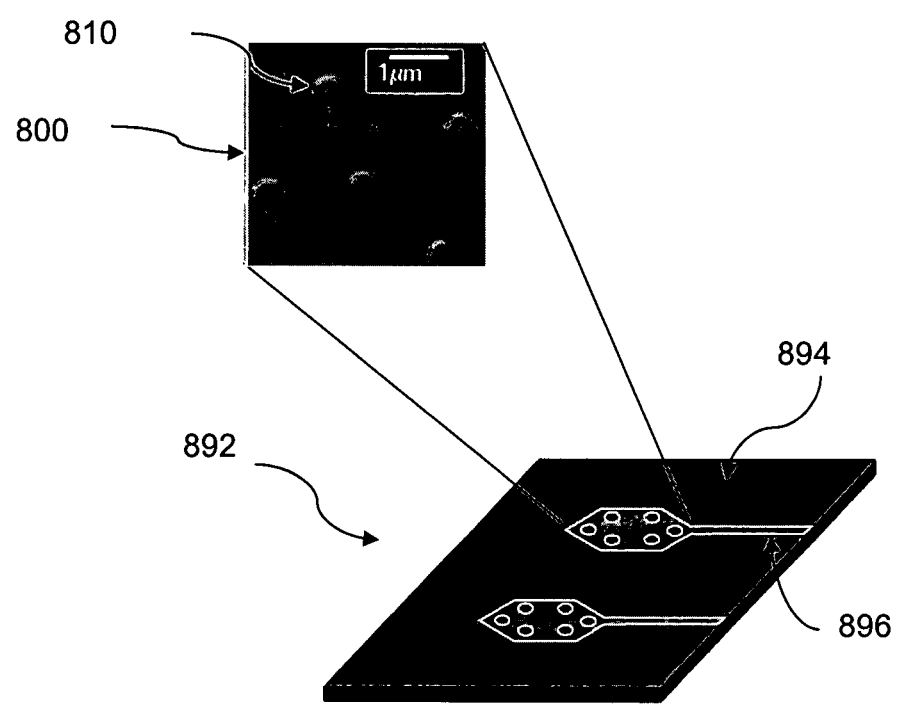

FIG. 8B shows a sensor device 892 comprising the nanoscale sensor array 800 containing individual unit structures 810. Optionally, the device 892 may be integrated with on-chip microfluidics. For example, a microfluidic inlet channel 894 provides a liquid solution to the array 800. After the solution has been tested for the presence of target species by the array 800, the solution is removed through a microfluidic outlet channel 896. Each unit structure 810 in a given array 800 may test for the same or different target species. The sensitivity of the device 892 is amplified by the number of unit structures 810 in the array 800, which, as shown in the inset SEM image in FIG. 8B, can be about $10^8/cm^2$ or less. The volume of solution provided to the array can be on the order of a few attoliters (1 aL=$10^{-18}$ L) or greater.

Figure 9A:
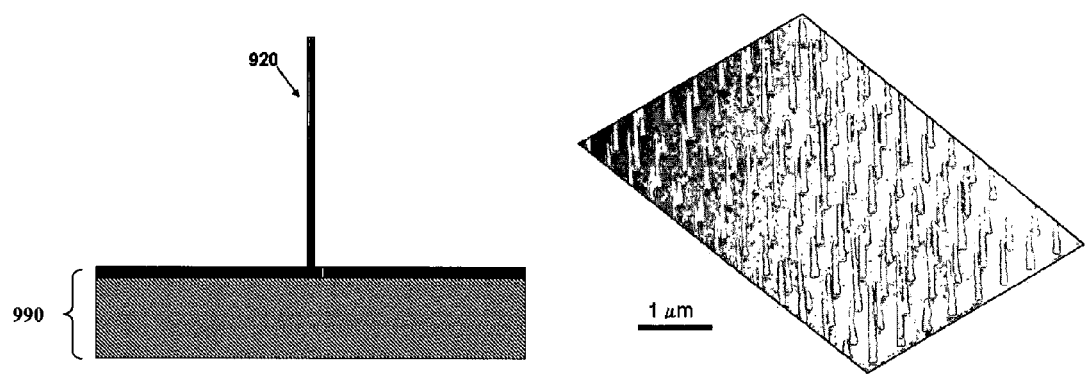
FIG. 9A-9F show the steps used for fabricating a nanoscale sensor according to an embodiment of the present invention.

FIG. 9A-9F show a method of making a nanoscale sensor apparatus according to an embodiment of the present invention. In FIG. 9A, catalyst particles, such as Ni nanodots, are deposited on a metallized substrate 990. In an embodiment, the metallized substrate 990 is a Si wafer coated with a metallic coating such as chromium. Carbon deposition is catalyzed underneath the Ni nanodots and forms a highly registered nanotube array with the presence of certain gasses, plasma, and high temperature (for simplicity, the schematic image shows a single nanotube 920). Typically, the nanotube 920 diameter is about 50-150 nm.

Figure 9B:
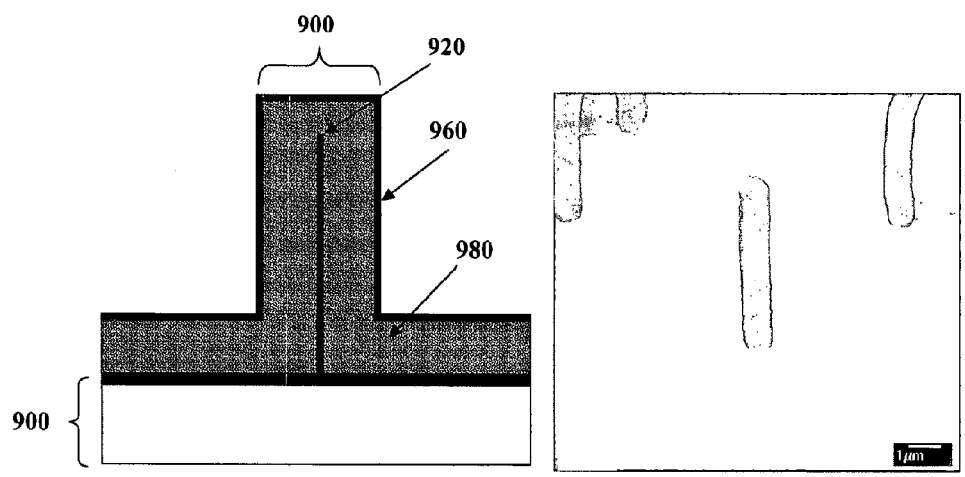

FIG. 9B shows a nanoscale coaxial transmission line 900 after the addition of a dielectric material 980 and a metallic layer 960 on the nanotube 920. In an embodiment, the dielectric material 980 is alumina and the metallic layer 960 is chromium. Depending on the size of the target molecule particles for detection, the dielectric 980 thickness can be adjusted from tens of nm to hundreds of nm, such as about 10 nm to about 500 nm. Both layers are deposited by sputter coating techniques.

Figure 9C:
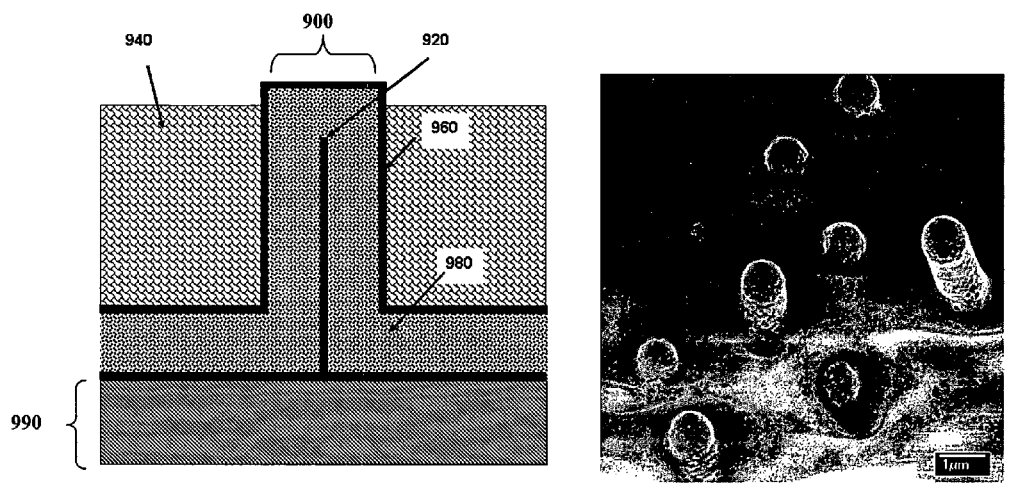

FIG. 9C shows the nanoscale coaxial transmission line 900 after spin-coating of a thick dielectric material 940. The dielectric material 940 should be biocompatible, insulative, stiff, water-resistant, and non-adhesive to biomolecules. In an embodiment, the dielectric material 940 is spin-on-glass (SOG). Alternatively, the material 940 is an epoxy, such as "Epon 828".

Figure 9D:
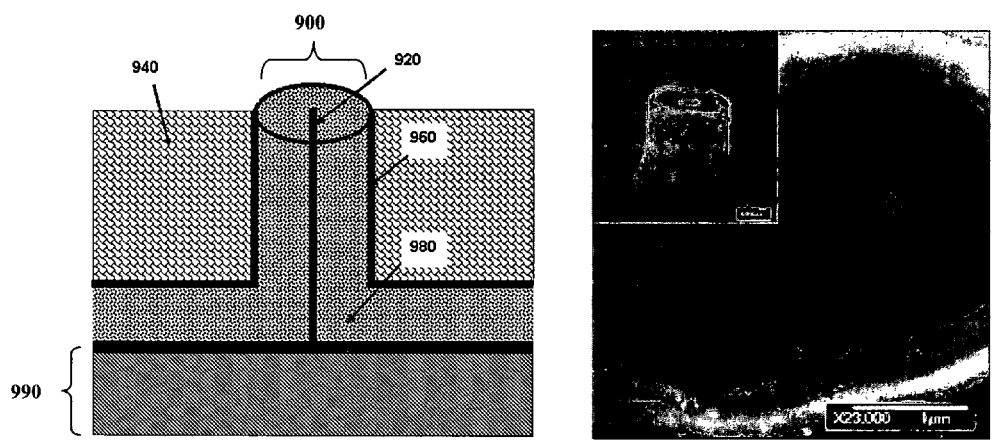

FIG. 9D shows the nanoscale coaxial transmission line 900 after mechanical polishing the tops of the nanoscale coaxial transmission lines 900 of FIG. 9C. The nanotube 920 in each nanoscale coaxial transmission line 900 has substantially the same length. Consequently, the capacitance of the nanoscale coaxial transmission line 900 will be close to the same.

Figure 9E:
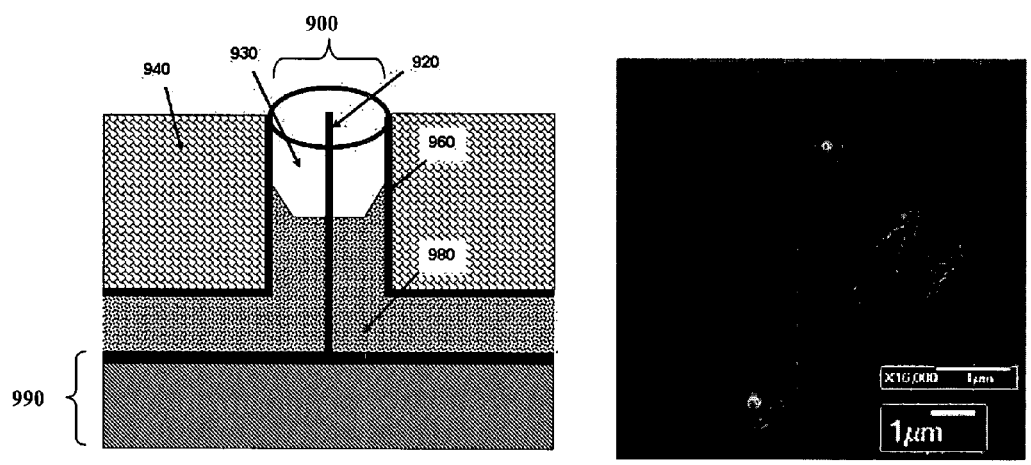

FIG. 9E shows the creation of nanocavities 930 in the nanoscale coaxial transmission lines 900. Nanocavities 930 are created by chemically etching the intermediate dielectric layer 980 between the nanotube 920 and the outer metal electrode 960. The nanocavity 930 provides size-dependent physical selection of target species entering into the nanocavity. The nanocavity is open at the top surface of the coaxial transmission line 900 to allow species having a size greater than the opening to enter into the nanocavity and to prevent species having a size greater than the opening from entering into the nanocavity. Significant impedance change will be produced corresponding to the capture of target species in the nanocavity 930. Partial etching of the dielectric layer 980 avoids nanotube 920 collapse due to surface tension. Preferably, etching is stopped before the nanotube 920 is shorted to the outer electrode 960. For example, the length of the nanotube 920 that is not surrounded by the dielectric layer 980 is about 50 nm to about 600 nm, such as about 100 nm to about 300 nm. In the high magnification SEM image in FIG. 9E, a developed cavity structure is broken on purpose to show the internal nanotube 920 component.

Figure 9F:
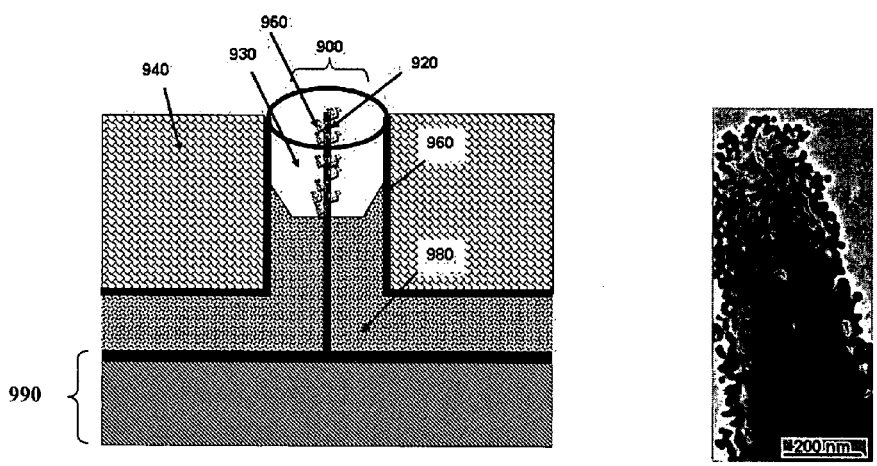

FIG. 9F shows the immobilization of sensing elements (e.g., molecules) 950 onto the top portion of the carbon nanotubes 920. Ferritin proteins were immobilized on the CNT by amide linkage, and the crystalline iron cores of the ferritin proteins are visible in the TEM image in FIG. 9F. The immobilization can be done by established covalent or non-covalent methods. The carbon nanotube 920 can be functionalized by chemical groups, or small molecules that carry the reactive groups, such as carboxylic acid, amine, and thiol groups. Functionalization can be performed by, for example, oxidation using a strong acid, nitrene addition, acrylation using diazonium salts, and 1,3-dipolar cycloadditions. For example, the carbon nanotube 920 is covalently functionalized with different types of small molecules to form the following molecular structures: 1) Ammonium-functionalized CNT; 2) Acetamido-functionalized CNT; 3) Fluorescein isothiocyanate (FITC)-functionalized CNT; 4) CNT bifunctionalized with ammonium and FITC; 5) CNT bifunctionalized with methotrexate (MTX) and FITC; 6) CNT bifunctionalized with amphotericin B (AmB) and FITC; 7) CNT bifunctionalized with ammonium and FITC. These groups will render the covalent linkages with the macromolecules. In a non-covalent version, for example, the chemical groups carry electro-charges and can facilitate the electrostatic attraction of macromolecules on to the nanotube 920 surface. In another embodiment, non-covalent immobilization is performed by an electropolymerization process to coat the CNTs with conductive (e.g., polypyrrole) and non-conductive (e.g., polyphenol) polymers. The thickness of the polypyrrole coating can be controlled by the deposition parameters. On the other hand, the polyphenol deposition process occurs by a self-limiting process which will stop once a compact and completely insulative coating is formed. The polymer coating can be doped with nanostructures (e.g., gold nanoparticles) or biomolecules (e.g., glucose oxidase which specifically binds to glucose). Another non-covalent strategy is based on the hydrophobic interaction. The nanotube 920 surface is originally hydrophobic. It is "sticky" to some macromolecules having hydrophobic residues. This mechanism can also be used to functionalize the nanotube 920 with small amphiphilic molecules. These molecules can be docked on the nanotubes 920 by its hydrophobic part. The hydrophilic end then can participate in the direct linkage or interaction with the macromolecules for immobilization. Many different CNT chemistries, including covalent and non-covalent chemistries, can be used to immobilize the active sensing elements on CNTs. For example, the methods described by D. Tasis et al., "Chemistry of Carbon Nanotubes," *Chem. Rev.* 106, 1105-1136 (2006) and K. Kostarelos et al., "Cellular uptake of functionalized carbon nanotubes is independent of functional group and cell type," *Nature Nanotechnology* 2, 108-113 (2006), all of which are incorporated herein by reference in their entirety, can be used.

A complete nanoscale sensing unit structure 900 will be finished upon the addition of active sensing elements 950 onto the top portion of the nanotubes 920. These active sensing elements 950 provide specific recognition of the sensing target species. The specificity is originated from the biological nature of biomolecule recognitions, such as antigen-antibody binding, complementary pairing of nucleotide molecules, targeted protein binding to certain DNA sequences, and specific catalytic activity to the chemical processes of their target molecules, etc. The sensor 900 will work in a fluidic environment that provides the compatibility to the biological activities of the molecules on nanotubes 920 or as the targets dissolved in the buffer.

The capture of the targeted species can be transduced to electric signals by the sensor 900 through different mechanisms, such as the changes in sensor impedance, capacitance, and Faradic current, etc. Detection can be performed by dielectric spectrometry, capacitance measurement (as of modified from that combined with patch clamp technique to measure femto fara level change in membrane capacitance), time-domain spectroscopy, waveguide resonators at THz frequencies, and electrochemical signals from the oxidant or reductant species in the nanocavity 930. The sensor 900 can detect biological processes occurring within the nanocavity 930, such as molecular redox reactions, enzyme catalyzed reactions, ligand-receptor and antigen-antibody interactions, DNA-protein binding and DNA stand duplexing.

A method of immobilizing sensing elements onto nanoscale coaxial transmission lines includes immersing an array of vertically aligned conductors of submicron to tens of microns in length supported on a metallized substrate in oxidative acids at room temperature overnight; rinsing the array with de-ionized water followed by critical point drying; sputtering the array with a dielectric material; sputtering the dielectric coated array with a metallic material to form external conductors; spin coating the array with about 1 to about tens of microns of insulating material; polishing the top of the array to expose a top portion of each of the conductors; immersing the array in etchant to partially etch off an area of dielectric material located at a top portion of the conductors to develop a nanocavity; immersing the array in a buffer solution to activate carboxyl groups on the conductors; adding in about 1 μg macromolecules containing primary amine groups to react with the functionalized conductors to form amide linkages; and rinsing the array with de-ionized water followed by critical point drying. In an embodiment, the array of vertically aligned conductors is an array of carbon nanotubes. In an embodiment, the oxidative acids may be about 0.5 M nitric acid or a mixture of 3 volume of 98% sulphric acid and 1 volume of 67% nitric acid. In an embodiment the dielectric material is sputtered onto the conductors at a thickness of about tens to about hundreds of a nanometer. In an embodiment, the metallic material is sputtered at a thickness of about 50 to about 200 nm. In an embodiment, the array is immersed in a buffer solution of about 0.1 M MES buffer (2-[N-morpholino]ethane sulfonic acid at pH 4.5) supplemented with 10 mg 1-ethyl-3-(3-dimethylaminopropyl)carbodiimide (EDC). In an embodiment, the etchant to partially etch off an area of dielectric material is a sodium hydroxide solution, for example 100 mM sodium hydroxide solution.

An alternative method of immobilizing sensing elements onto nanoscale coaxial transmission lines includes depositing gold onto an upper portion of an array of vertically aligned conductors of submicron to tens of microns in length supported on a metallized substrate by e-beam deposition; sputtering the array with a dielectric material; sputtering the dielectric coated array with a metallic material to form external conductors; spin coating the array with about 1 to about tens of microns of insulating material; polishing the top of the array to expose a top portion of each of the conductors; immersing the array in etchant to partially etch off an area of dielectric material located at a top portion of the conductors to develop a nanocavity; incubating the array with 1 μg thiol modified macromolecules; and rinsing the array with de-ionized water followed by critical point drying. In an embodiment, the array of vertically aligned conductors is an array of carbon nanotubes. In an embodiment the dielectric material is sputtered onto the conductors at a thickness of about tens to about hundreds of a nanometer. In an embodiment, the metallic material is sputtered at a thickness of about 50 to about 200 nm. In an embodiment, the etchant to partially etch off an area of dielectric material is 100 mM sodium hydroxide solution. In an embodiment, the array is immersed in about 100 mM sodium hydroxide for about five minutes. In an embodiment the array is incubated with thiol modified macromolecules for about two hours.

An alternative method of immobilizing sensing elements onto nanoscale coaxial transmission lines includes immobilizing intermediate macromolecules with certain biorecognition properties to the bioreactive macromolecules, which are in charge of capturing the target bio-species. In an embodiment, the intermediate macromolecule is one of DNA probe, PNA (peptide nucleic acid) probe, aptamer, antibody, avidin, streptavidin, positively charged polymer, and/or negatively charged polymer. In an embodiment, the bioreactive macromolecule carries the ligand of the intermediate macromolecules, such as DNA, protein, biotin, or certain electric charge.

An alternative method of immobilizing sensing elements onto nanoscale coaxial transmission lines includes depositing gold onto an upper portion of an array of vertically aligned conductors supported on a metallized substrate by e-beam deposition; sputtering the array with a dielectric material; sputtering the dielectric coated array with a metallic material to form external conductors; spin coating the array with about 1 to about 10 micron of insulating material; polishing the top of the array to expose a top portion of each of the conductors; immersing the array in sodium hydroxide to partially etch off an area of dielectric material located at a top portion of the conductors to develop a nanocavity; incubating the array with streptavidin or thiol modified streptavidin to covalently link the macromolecules to the conductors; and rinsing the array with de-ionized water followed by critical point drying. In an embodiment, the array of vertically aligned conductors is an array of carbon nanotubes. In an embodiment the dielectric material is sputtered onto the conductors at a thickness of about tens to about hundreds of a nanometer. In an embodiment, the metallic material is sputtered at a thickness of about 50 to about 200 nm. In an embodiment, the array is immersed in about 100 mM sodium hydroxide for about five minutes. In an embodiment the array is incubated with thiol modified macromolecules for about two hours.

An alternative method of immobilizing sensing elements onto nanoscale coaxial transmission lines includes immersing an array of vertically aligned conductors supported on a metallized substrate in oxidative acids at room temperature overnight; rinsing the array with de-ionized water followed by critical point drying; sputtering the array with a dielectric material; sputtering the dielectric coated array with a metallic material to form external conductors; spin coating the array with about 1 to about 10 micron of insulating material; polishing the top of the array to expose a top portion of each of the conductors; immersing the array in sodium hydroxide to partially etch off an area of dielectric material located at a top portion of the conductors to develop a nanocavity; immersing the array in a buffer solution to activate carboxyl groups on the conductors; adding in amine enriched polymers to conduct aminization between the polymer and the conductors; rinsing the array with de-ionized water; transferring the array to neutral sodium chloride solution with about 1 μg macromolecules that carry negative charges at a pH of 7.0; incubating the array for about thirty minutes; and rinsing the array with sodium chloride solution followed by critical point drying. In an embodiment, the array of vertically aligned conductors is an array of carbon nanotubes. In an embodiment, the oxidative acids may be about 0.5 M nitric acid or a mixture of 3 volume of 98% sulphric acid and 1 volume of 67% nitric acid. In an embodiment the dielectric material is sputtered onto the conductors at a thickness of about tens to about hundreds of a nanometer. In an embodiment, the metallic material is sputtered at a thickness of about 50 to about 200 nm. In an embodiment, the array is immersed in a buffer solution of about 10 ml 0.1 M MES buffer (2-[N-morpholino] ethane sulfonic acid at pH 4.5) supplemented with 10 mg 1-ethyl-3-(3-dimethylaminopropyl)carbodiimide (EDC). In an embodiment the amine enriched polymer is about 10 μl polylysine (0.01%, 70 Kd-140 Kd).

In an embodiment, goat anti-human antibody is immobilized on a nanoscale sensor of the presently disclosed embodiments, which enables the capture of human IgG target species in a solution. Impedance Spectroscopy measurements are performed with a Solartron 1470 Battery Test Unit and a Solartron 1255 B Frequency Response Analyzer (Solartron Inc., UK) for 2.5 mM $K_4[Fe(CN)_6]$+2.5 mM $K_3[Fe(CN)_6]$ in 0.1 M KCl+10 mM PBS (phosphate buffered saline) (pH 7.0) solution for the electrochemical detection of human IgG. A sinusoidal potential modulation of ±5 mV amplitude is superimposed on the formal potential of the redox couple of $[Fe(CN)_6]^{4-}/[Fe(CN)_6]^{3-}$ (0.22 V vs. Ag/AgCl). The redox couple provides a background impedance subject to be disturbed by the IgG binding. The change in the impedance is calculated and transformed based on the amount of molecular bindings. The impedance data may be fitted to the electrical equivalent circuit shown in FIG. 1B using the Zplot/Zview software (Scribner Associates Inc.). The equivalent circuit provides an electrical analogue of chemical/physical processes probed by Electrochemical Impedance Spectroscopy. Electrolyte solutions are deoxygenated by bubbling with high-purity nitrogen for at least 20 min. All measurements are carried out at room temperature.

Figure 10:
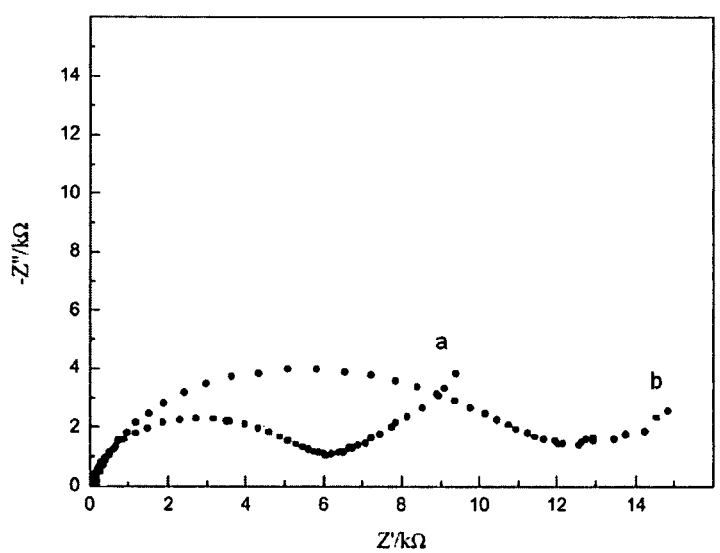
FIG. 10 shows a complex impedance (Nyquist) plot of a nanoscale sensor immobilized with goat anti-human antibody and the response to antigen, human IgG, binding. Trace a and b are the results before and after IgG binding.

In order to capture human IgG, the nanoscale sensor is immersed in a pH 7.0 phosphate buffer containing various concentrations of antigen, i.e. human IgG, at 37° C. for 30 min, followed by the rinsing of the nanoscale sensor in 0.01 M PBS (pH 7.0) solution to remove any unbound antigen. Impedance Spectroscopy measurements were then performed, and the results are illustrated by using a Nyquist plot, of which each point is the impedance at one frequency. A similar plot is shown in FIG. 10. The semicircle diameter will increase with the human IgG concentration, signifying that more amount of antigen was linked to the interface, and generating a larger inter-electrode resistance and stronger blocking to the electron transfer of the redox probe.

A typical shape of an electrochemical impedance spectrum includes a semicircle region lying on the Z axis and followed by a straight line. The semicircle portion, observed at higher frequencies, corresponds to the electron-transfer limited process, whereas the linear part is characteristic of the lower frequencies range and represents the diffusional limited electron-transfer process. In the case of a very fast electron-transfer process, the impedance spectrum could include only the linear part, whereas a very slow electron-transfer step results in a big semicircle region that is not accompanied by a straight line. The electron-transfer kinetics and diffusional characteristics can be extracted from the spectra.

Figure 11:
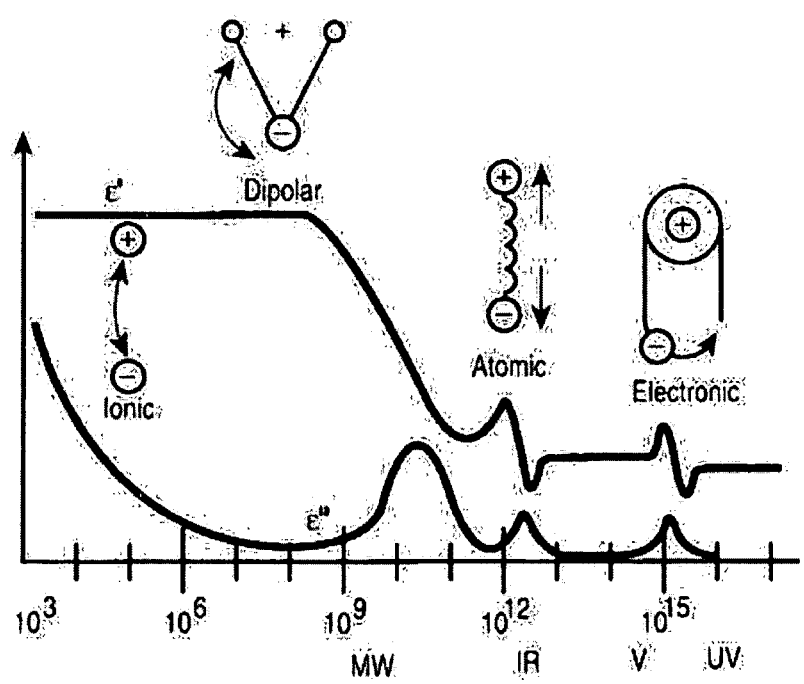
FIG. 11 shows a dielectric permittivity spectrum over a wide range of frequencies. The real and imaginary parts of permittivity are shown, and various processes are depicted: ionic and dipolar relaxation, and atomic and electronic resonances at higher energies.

As stated above, the equivalent circuit of FIG. 10 suggests the approach for detecting target species is Impedance Spectroscopy or Dielectric Spectroscopy. There are a number of different dielectric mechanisms, connected to the way a studied medium reacts to the applied field, as shown in FIG. 11. Each dielectric mechanism is centered around its characteristic frequency, which is the reciprocal of the characteristic time of the process. In general, dielectric mechanisms can be divided into relaxation and resonance processes. The most common, starting from high frequencies, are 1) Electronic polarization, this resonant process occurs in a neutral atom when the electric field displaces the electron density relative to the nucleus it surrounds; 2) Atomic polarization is observed when an agglomeration of positive and negative ions is deformed under the force of the applied field. This is also a resonant process; 3) Dipole relaxation, which originates from permanent and induced dipoles aligning to an electric field. Their orientation polarization is disturbed by thermal noise (which dis-aligns the dipole vectors from the direction of the field), and the time needed for dipoles to relax is determined by the local viscosity. These two facts make dipole relaxation dependant on temperature and chemical surrounding; and 4) Ionic relaxation, which is comprised of ionic conductivity and interfacial and space charge relaxation. Ionic conductivity predominates at low frequencies and introduces only losses to the system. Interfacial relaxation occurs when charge carriers become trapped at interfaces of heterogeneous systems.

Dielectric Spectroscopy has been used in materials science, and also in studying the electrical properties of biological materials. Impedance Spectroscopy is gaining renewed strength as a tool complementary to other techniques used to study the structural and related properties of proteins by providing important information about the protein's charge dynamics, as related to its structure. Impedance Spectroscopy is sensitive to polarization interfaces and intermolecular interactions, such as dipole-dipole interactions and cooperative processes.

Figure 12:
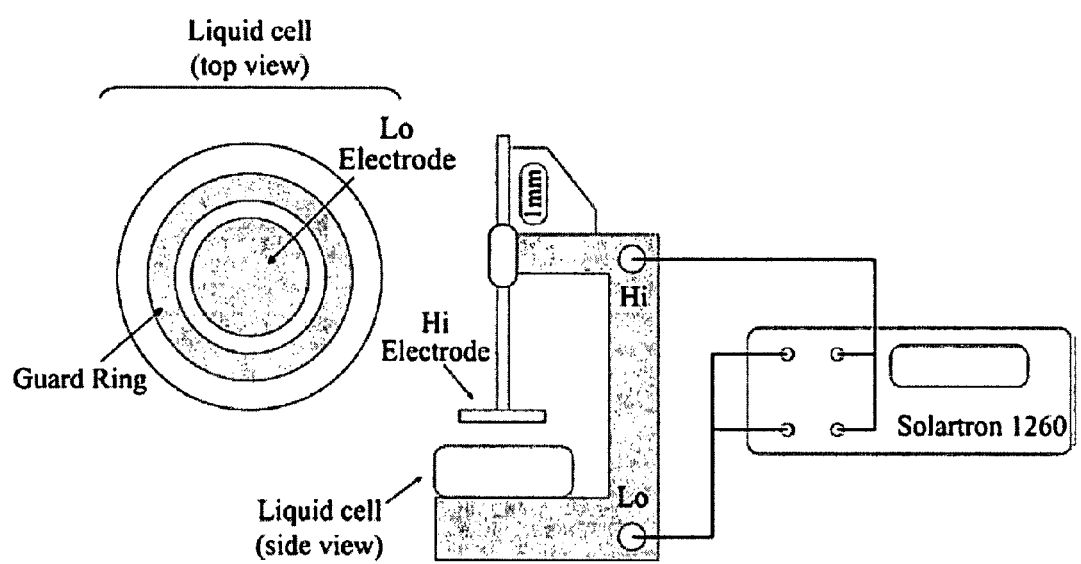
FIG. 12 shows an experimental setup of an Impedance Spectroscopy (1S) apparatus that may be used with the nanoscale ultrasensitive sensor unit structure according to an embodiment of the present invention.

FIG. 12 shows an experimental setup for Impedance Spectroscopy. For example, a Solartron 1260 impedance/gainphase analyzer is used to sweep the frequency over a range of about 1 Hz to about 1 MHz. The liquid cell with stainless steel electrodes was 2 cm in diameter, and contained a guard ring that reduced fringing fields. The separation distance used in the experiments between the electrodes was 1 mm.

$$\Delta \varepsilon = (\varepsilon_{s'} - \varepsilon_{\infty}) = \frac{g\mu^2 N_A C}{2\varepsilon_0 MkT} \quad (3)$$

Equation (3) tells us that, by measuring the low- and high-frequency-limiting dielectric constants, $\varepsilon_s$ and $\varepsilon_\infty$, one can calculate the dipole moment of the protein for given assumptions of g, thereby, to determine its identity based on the fingerprint. This relationship has been used for extracting with high accuracy the electrical dipole moment for other biomolecules, such as myoglobin, hemoglobin, DNA, etc. $\mu$ is the dipole moment of the protein, $N_A$ is Avogadro's number, C is the concentration in (mg/ml), M is the mass of the protein (kg/mol), k is the Boltzmann constant, T the absolute temperature, and g is the Kirkwood correlation factor, which is usually assumed to be 1.

Time Domain Dielectric Spectroscopy (TDDS) is based on the transmission line theory in the time domain and studies the heterogeneity in the coaxial lines according to the change in shape of a test signal. In this method a rapidly increasing voltage step arrives at the sampling head where the signal reflected from the dielectric sample is also registered. For the ideal system, the voltage applied to the sample is:

$$V(t) = V_o(t) + V_r(t)$$

where $V_o(t)$ and $V_r(t)$ are the incident and reflected signals, respectively. The expression for the flow of current through the sample is $$I(t) = \frac{1}{Z_0}[V_0(t) - R(t)]$$

where $Z_0$ is the characteristic impedance of the transmission line in the absence of a target specie between the conductors.

As long as the transmission line is homogeneous, the shape of this pulse will not change. But, in the case of heterogeneity in the line (for example, when a target specie is present between the conductors) the signal is partly reflected from the air-dielectric interface and partly passes through it. Dielectric measurements are made along a coaxial transmission line with the sample mounted in a sample cell that terminates the line.

FIG. 12 illustrates the experimental set-up used for the TDDS method according to an embodiment of the present invention. The recorded signals are shown in FIGS. 13 and 14.

Figure 13:
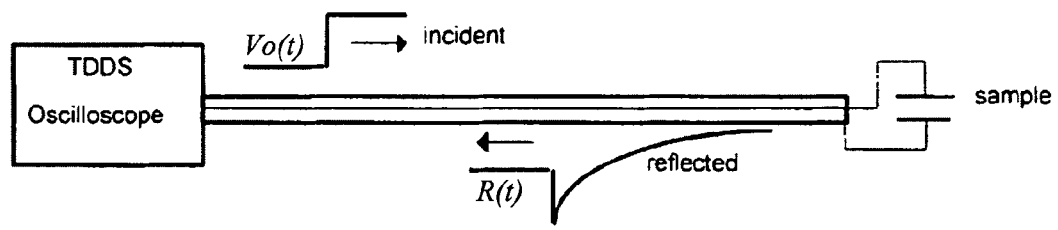
FIG. 13 shows a simplified block diagram of the set-up common for most Time Domain Dielectric Spectroscopy (TDDS) methods.

FIG. 13 is an illustration of the basic principles of the TDDS system, where $V_0(t)$ is the incident pulse and R(t) is the reflected signal.

Figure 14:
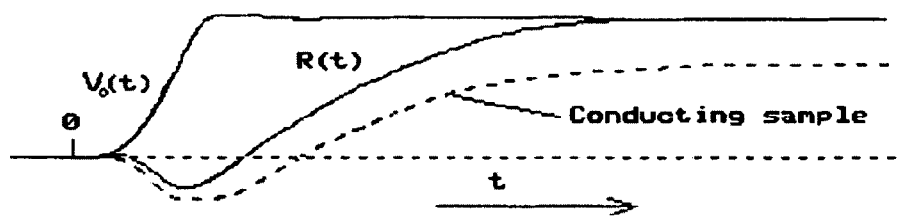
FIG. 14 shows the characteristic shape of the signals recorded during a TDDS experiment as shown in FIG. 13.

FIG. 14 shows the characteristic shape of the signals recorded during a TDDS experiment.

The low-frequency conductivity ($\sigma$) of the sample can be determined directly in time domain. Here, $\varepsilon_0 = 8.85 \times 10^{-12}$ F/m, and $C_0$ is the electric capacity of the coaxial sample cell terminated to the coaxial line.

$$\sigma = \frac{\varepsilon_0}{Z_0 C_0} \lim_{t \to \infty} \frac{V_0(t) - R(t)}{V_0(t) + R(t)}$$

FIG. 15A-15D are SEM images showing the steps used to fabricate an ordered pattern of nanocoaxial sensors according to an embodiment of the present invention. FIG. 15A shows a self-assembled mask of polystyrene nanospheres deposited on a substrate. E-beam deposition was used to deposit Ni catalyst in the interstices of the nanosphere mask. FIG. 15B shows the Ni catalyst after it was annealed to form a hexagonal pattern of Ni nanodots on the substrate surface. FIG. 15C shows the surface after CVD was performed to grow vertically-aligned CNTs at the catalyst, sites. FIG. 15D shows an array of completed nanocoaxial sensors after the dielectric and outer conductors were deposited onto the CNTs. The distance between each nanocoaxial sensor can be adjusted by varying the size of the nanospheres. Other types of masks having different patterns can also be used. The spatial amplification of the nanosensor array can be adapted to scale linearly with the number of nanosensors in the array. For example, the array is group addressable. In an embodiment, the individual nanocoaxial sensors in an array are connected in parallel and the total capacitance of the array is the sum of the capacitance of each individual nanocoaxial sensor. In another embodiment, the individual nanocoaxial sensors in an array are connected in series and the total capacitance of the array is the inverse of the sum of the inverse capacitance of each individual nanocoaxial sensor.

FIG. 16A-16D show the precise placement and spatial arrangement of an ordered arrangement of CNTs formed on tungsten leads. FIGS. 16A and 16B are SEM images of tungsten leads formed on a Si substrate. The tips of the tungsten leads are spaced apart from each other, with gaps ranging from about 40 nm to about 1 μm. A single Ni catalyst nanodot having a diameter of about 100 nm is deposited on the tip of each lead, as shown in FIG. 16B. FIG. 16C shows an AFM image of the same leads. FIG. 16D is a SEM image of the leads after CNTs are grown from the Ni catalyst nanodots. Nanocoaxial sensors are formed around each CNT by depositing a dielectric and an outer metal layer around each CNT. Each nanocoaxial sensor in the array can operate independently of the others in the array. For example, the inner conductor of each sensor is not in electrical contact with any other inner conductor in the array, allowing each inner conductor to be probed at a different bias. The independently addressable array of nanocoaxial sensors allows multiplexing of the signal being provided by each sensor.

FIG. 17 shows four SEM images of nanocoaxial sensors having different sized nanocavity openings according to an embodiment of the present invention. The distance between the inner conductor and the outer conductor can be tuned by changing diameter of the inner conductor or the thickness of the dielectric material, or both. For example, when a CNT is used as the inner conductor, the diameter of the CNT can be controlled by the size of the catalytic Ni particle used. Also, the thickness of the dielectric material is controlled by the duration of the magnetron sputtering deposition. The depth of the nanocavity can be tuned by etching the dielectric material with different etchants or by varying the duration of the etching step, or both. The CNT diameter can be adjusted from about 40 nm to about 200 nm. The thickness of the dielectric can be adjusted from about 10 nm to about 500 nm. The depth of the nanocavity can be adjusted from about 50 nm to about 2000 nm. The nanocavity is adapted to exhibit a size-dependent physical selection of target species entering into the nanocavity. The size of the nanocavity opening is adjusted depending on the size of the target species to be detected by the nanocoaxial sensor. For example, a size of the nanocavity opening is selected such that substantially no molecules having a size greater than a critical size will enter into the nanocavity. The critical size is determined for a given target species, for example, by applying differently-sized target species, such as *E. coli* (ranging 0.5×1.5 µm to 0.8×2.2 µm) or SARS-CoV (ranging diameter 60 nm to 120 nm), to an array of nanocoaxial sensors of known opening size.

The nanocavities of the present invention are compatible with various methods for filling the nanocavities with solution. For example, the nanocavities are filled with solution by capillary action, whereby the nanocavity surface (e.g., the walls of the outer and/or inner conductors within the nanocavity) effectively draw the solution into the nanocavity by hydrophobic/hydrophilic interactions. Capillay action is optimized by judicious choice of conductor materials and carrier solvent. In addition, the solution can be drawn into the nanocavity by an electrowetting process, whereby an electrical potential is applied to the inner and/or outer conductors. For example, the electrowetting method described in an article by J. Y. Chen et al., "Electrowetting in Carbon Nanotubes," *Science* 310, 1480-1483 (2005), which is incorporated herein by reference in its entirety, can be used. Optionally, a supercritical filling process can be performed, including first filling the nanocavity with liquid carbon dioxide and then filling the nanocavity with the solution by substitution. For example, the supercritical filling process described in the article by X. B. Wang et al., "Nanofluids in carbon nanotubes using supercritical CO 2: a first step towards a nanochemical reaction," *Applied Physics A* 80, 637-639 (2005), which is incorporated herein by reference in its entirety, can be used. The target species can be labeled with magnetic and/or electrically charged nanoparticles and drawn into the nanocavities by magnetic and/or electrostatic attraction to complementary nanoparticles that are immobilized within the nanocavities. In an embodiment, the target species are magnetically and/or electrostatically drawn to the target species. Optionally, if CNTs are used as the inner conductors, an electrical potential is applied to the CNTs to enhance the electrostatic attraction.

Figure 18A:
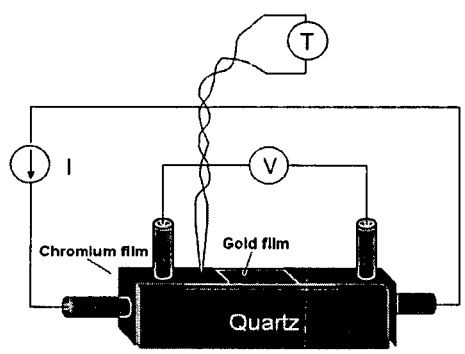
FIG. 18A-18C shows gold film nucleation and CNT functionalization according to an embodiment of the present invention.
Figure 18B:
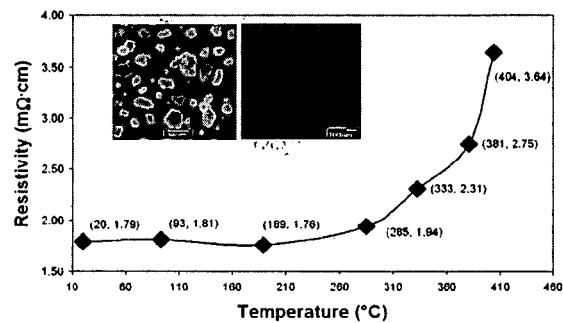

FIG. 18 shows nucleation of a gold film and CNT functionalization according to an embodiment of the present invention. FIG. 18A shows the experimental setup in which a gold film deposited on a quartz substrate was heated at a temperature (T) while its resistivity (mΩ·cm) was measured. FIG. 18B shows that the resistivity of the gold film increased exponentially as the temperature was increased from 270° C. to 450° C., above which the resistivity became to large to be measured, thus indicating the loss of electrical connection between the two electrodes. The inset of FIG. 18B shows SEM images of the gold film before (right) and after (left) the thermal anneal. As can be seen, the gold film nucleated into discreet and electrically isolated gold nanoparticles.

Figure 18C:
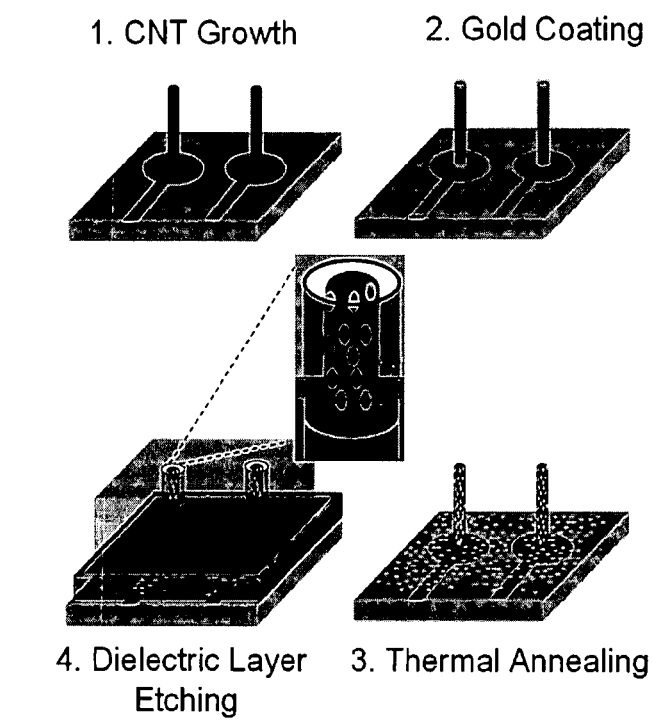

FIG. 18C shows a method of functionalizing CNTs with gold nanoparticles. First, CNTs are grown by CVD or other suitable method on patterned electrodes, such as on the tungsten leads shown in FIG. 16A-16D. Second, the CNTs are coated with a gold film having a thickness of about 1 nm to about 12 nm by thermal or electron beam evaporation. Third, the gold film is annealed at a temperature greater than about 450° C., such as about 500° C. to about 650° C. for 45 min in a horizontal tube furnace with constant flowing Ar gas (50 sccm) and pressure of 5 Torr. The gold film is broken into discrete nanoparticles, and the CNTs grown on different electrodes are not in electrical contact with each other. Fourth, the gold-functionalized CNTs are coated with a dielectric material and then coated with an outer metal layer. At least a portion of the dielectric material is etched away to form a nanocavity and to reveal the gold nanoparticle-functionalized CNT. These gold nanoparticles are available for subsequent chemistries. For example, an anti-Fcγ antibody is modified with a thiol group through a C7 crank and is then bound to the gold nanoparticle-functionalized CNT. A secondary antibody (anti-SARS mAb) is then bound to the anti-Fc-γ antibody for selective capture of SARS-CoV virus.

The foregoing description of the invention has been presented for purposes of illustration and description. It is not intended to be exhaustive or to limit the invention to the precise form disclosed, and modifications and variations are possible in light of the above teachings or may be acquired from practice of the invention. The description was chosen in order to explain the principles of the invention and its practical application. It is intended that the scope of the invention be defined by the claims appended hereto, and their equivalents.

What is claimed is:

1. An apparatus comprising:
a first nanocoaxial sensor, comprising:
an outer conductor having a first longitudinal axis;
an inner conductor having a second longitudinal axis coaxial with the first longitudinal axis;
a nanocavity, defined by an inner surface of the outer conductor and an outer surface of the inner conductor, sized to allow target species to enter the nanocavity between the outer and inner conductors; and
an active sensing element immobilized within the nanocavity on at least one of the inner or outer conductors, wherein the active sensing element is adapted to selectively capture at least one of the target species.

2. The apparatus of claim 1, wherein:
the outer conductor circumferentially surrounds the inner conductor; and
the nanocavity is located at one end of the nanocoaxial sensor between the inner and outer conductors.

3. The apparatus of claim 2, wherein the outer conductor comprises a cylinder and the inner conductor comprises a nanofiber.

4. The apparatus of claim 3, wherein:
the inner conductor is about 40 nm to about 200 nm in diameter; and
the nanocavity is about 50 nm to about 2,000 nm in depth measured from the one end of the nanocoaxial sensor.

5. The apparatus of claim 2, wherein the inner conductor is in electrical contact with a metal layer deposited on at least a portion of a substrate and the inner conductor is substantially perpendicular to the substrate.

6. The apparatus of claim 5, wherein the outer conductor is not in electrical contact with the metal layer.

7. The apparatus of claim 1, further comprising a dielectric material that circumferentially surrounds a portion of the inner conductor, wherein:
the outer conductor comprises a conductive metal oxide;
the inner conductor comprises a metal alloy.

8. The apparatus of claim 7, wherein the inner conductor comprises a carbon fiber.

9. The apparatus of claim 8, wherein:
the dielectric material comprises at least one of $Al_2O_3$, and a non-conductive polymer;
the outer conductor comprises a transition metal; and
the carbon fiber comprises a carbon nanotube.

10. The apparatus of claim 9, wherein:
the transition metal comprises chromium;
the carbon nanotube comprises a multi-walled carbon nanotube;

the dielectric material comprises $Al_2O_3$;
the nanocavity comprises an etched cavity in at least a portion of the dielectric material; and
the active sensing element is immobilized within the nanocavity on at least a portion of the multi-walled carbon nanotube.

11. The apparatus of claim 1, further comprising one or more nanocoaxial sensors, wherein:
the first and the additional nanocoaxial sensors form a sensor array; and
each of the additional nanocoaxial sensors comprises:
an outer conductor having a first longitudinal axis;
an inner conductor having a second longitudinal axis coaxial with the first longitudinal axis;
a nanocavity, defined by an inner surface of the outer conductor and an outer surface of the inner conductor, sized to allow target species to enter the nanocavity between the outer and inner conductors; and
an active sensing element immobilized within the nanocavity on at least one of the inner or outer conductors, wherein the active sensing element is adapted to selectively capture at least one of the target species.

12. The apparatus of claim 11, wherein the array comprises an ordered pattern of the sensors on a substrate.

13. The apparatus of claim 12, wherein the ordered pattern comprises a hexagonal pattern.

14. The apparatus of claim 11, wherein the inner conductor of at least one sensor is functionalized with gold nanoparticles but is not in electrical contact with the inner conductor of at least one other sensor.

15. The apparatus of claim 11, further comprising an insulative material disposed between the outer conductors of adjacent nanosensors.

* * * * *